US012781234B2

(12) United States Patent
Zhang et al.

(10) Patent No.: US 12,781,234 B2
(45) Date of Patent: Nov. 3, 2026

(54) **ENGINEERED *SACCHAROMYCES CEREVISIAE* STRAINS FOR PRODUCTION OF VANILLYLAMINE AND CAPSAICIN, AND CONSTRUCTION METHOD AND USE THEREOF**

(71) Applicant: SHIHEZI UNIVERSITY, Shihezi (CN)

(72) Inventors: Genlin Zhang, Shihezi (CN); Yuanyuan Li, Shihezi (CN); Jinyu Zhao, Shihezi (CN); Di Qiu, Shihezi (CN); Yan Zhang, Shihezi (CN)

(73) Assignee: SHIHEZI UNIVERSITY, Xinjiang (CN)

( * ) Notice: Subject to any disclaimer, the term of this patent is extended or adjusted under 35 U.S.C. 154(b) by 385 days.

(21) Appl. No.: 18/522,708

(22) Filed: Nov. 29, 2023

(65) Prior Publication Data

US 2024/0294929 A1 Sep. 5, 2024

Related U.S. Application Data

(63) Continuation of application No. PCT/CN2023/086755, filed on Apr. 7, 2023.

(30) Foreign Application Priority Data

Mar. 1, 2023 (CN) ......................... 202310194657.5

(51) Int. Cl.

| | |
|---|---|
| ***C12N 15/81*** | (2006.01) |
| ***C12N 1/19*** | (2006.01) |
| ***C12P 7/22*** | (2006.01) |
| ***C12P 7/24*** | (2006.01) |
| ***C12P 7/40*** | (2006.01) |
| ***C12P 13/00*** | (2006.01) |
| ***C12P 13/02*** | (2006.01) |

(52) U.S. Cl.

CPC ................ *C12N 15/81* (2013.01); *C12P 7/22* (2013.01); *C12P 7/24* (2013.01); *C12P 7/40* (2013.01); *C12P 13/001* (2013.01); *C12P 13/02* (2013.01)

(58) Field of Classification Search

None

See application file for complete search history.

(56) References Cited

U.S. PATENT DOCUMENTS

| | | | | |
|---|---|---|---|---|
| 9,951,358 | B2 * | 4/2018 | Chen | C12N 9/1029 |
| 11,459,591 | B2 * | 10/2022 | Chen | C12N 9/1051 |
| 2011/0166371 | A1 | 7/2011 | Kisaka et al. | |
| 2019/0010522 | A1 | 1/2019 | Chen et al. | |
| 2019/0390231 | A1 | 12/2019 | Chen et al. | |
| 2021/0317485 | A1 | 10/2021 | Chen et al. | |
| 2025/0019727 | A1 * | 1/2025 | Roussel | C12N 9/16 |

FOREIGN PATENT DOCUMENTS

| | | | |
|---|---|---|---|
| CN | 105907804 | A | 8/2016 |
| WO | 2015193348 | A1 | 12/2015 |

OTHER PUBLICATIONS

Zhao et al., Yeast-Based Whole-Cell Factory for the Ecofriendly Synthesis of Vanillylamine as a Critical Step toward Capsaicin Production, ACS Sustainable Chem. Eng. May 11, 2023, 7683-91. (Year: 2023).*

Qiu et al., De novo biosynthesis of vanillin in engineered *Saccharomyces cerevisiae*, Chem. Eng. Sci. 263, 2022, 118049. (Year: 2022).*

Masai et al., Cloning and Characterization of the Ferulic Acid Catabolic Genes of *Sphingomonas paucimobilis* SYK-6, Appl. Environ. Microbiol. 68, 2002, 4416-24. (Year: 2002).*

International Search Report, PCT/CN2023/086755, Nov. 19, 2023, 4 pages.

Aza-Gonzalez et al., Molecular biology of capsaicinoid biosynthesis in chili pepper (*Capsicum* spp.), Plant Cell Rep (2011) 30: pp. 695-706.

* cited by examiner

*Primary Examiner* — Todd M Epstein

(74) *Attorney, Agent, or Firm* — Edell, Shapiro & Finnan, LLC

(57) ABSTRACT

The present disclosure provides engineered *Saccharomyces cerevisiae* strains for production of vanillylamine and capsaicin, and a construction method and use thereof, and belongs to the technical field of bioengineering. In the present disclosure, a synthesis pathway of vanillylamine is expressed heterologously in *Saccharomyces cerevisiae* for the first time, and biosynthesis of the vanillylamine is realized for the first time. After the optimization of precursors supply and the optimization of S-adenosyl-L-methionine (SAM) cycle, a yield of the vanillylamine reaches 16.48 g/L, and a synthesis efficiency of the vanillylamine is increased by nearly 155%. This is the highest optimization efficiency obtained by optimizing the SAM cofactor strategy so far.

15 Claims, 4 Drawing Sheets

Specification includes a Sequence Listing.

| | Z2 | Z3 | Z4 | Z5 | Z7 | Z8 |
|---|---|---|---|---|---|---|
| Vanillylamine Pathway | + | + | + | + | + | + |
| Phenylalanine Pathway | - | + | - | - | + | + |
| SAM Pathway-*S.cerevisiae* | - | - | + | - | + | - |
| SAM Pathway-*E.coli* | - | - | - | + | - | + |

SEQUENCE LISTING

```
Sequence total quantity: 144
SEQ ID NO: 1            moltype = DNA  length = 2154
FEATURE                 Location/Qualifiers
source                  1..2154
                        mol_type = other DNA
                        note = nucleotide sequence of synthesized PAL2
                        organism = synthetic construct
SEQUENCE: 1
atggaccaaa ttgaggcaat gttgtgcggt ggtggtgaaa aaacaaaggt cgcagtcaca  60
actaaaacat tagctgatcc attgaactgg ggtttggctg ctgaccaaat gaagggttct  120
catttagatg aagtcaaaaa gatggtcgag gagtatagga gaccagtcgt caacttggga  180
ggtgagacat tgacaattgg tcaagttgca gcaatttcta ctgtcggagg ttcagttaaa  240
gtcgagttgg ctgagacatc tagagctgga gtcaaggctt catcagactg ggtcatggaa  300
tctatgaata aaggtacaga ttcatacggt gtcactactg gtttcggtgc tacttctcat  360
```

-continued

```
agaagaacaa agaacggaac agctttgcaa acagaattga ttagattttt gaatgctggt  420
attttcggaa atacaaaaga aacttgtcat acattgcctc agtctgctac aagagctgct  480
atgttggttc gtgtcaacac attgttgcaa ggttattctg gtataagatt tgaaatttta  540
gaagctataa catctttatt aaatcataat atttctccat ctttgccttt gagaggtact  600
attacagcat ctggagattt agttccatta tcatacattg ctggtttgtt gactggtagg  660
cctaactcaa aggcaactgg tcccgatggt gagtcattga ctgctaaaga ggctttcgaa  720
aaagctggta tatctactgg tttcttcgac ttgcaaccaa aggagggttt ggcattggtc  780
aacggtactg ctgttggttc tggtatggct tcaatggttt tatttgaagc aaatgttcaa  840
gctgttttgg cagaggtctt gtctgcaatt ttcgctgagg ttatgtctgg taagcccgaa  900
tttactgacc atttgactca tagattaaag catcatcccg gtcaaattga agcagctgct  960
attatggaac acattttgga tggttcttct tacatgaaat tggctcagaa ggttcatgag  1020
atggacccat tgcagaagcc aaagcaagat aggtacgctt tgagaacttc accacagtgg  1080
ttgggtccac agattgaagt tataagacaa gctactaaat ctatagaaag agaaattaat  1140
tcagttaacg ataatccatt gattgatgtt tcaagaaata aggctattca tggtggtaat  1200
tttcaaggta ctccaattgg tgtttctatg gataatacta gattggctat tgcagcaatt  1260
ggtaagttaa tgtttgcaca attctcagaa ttagttaacg atttttataa taacggtttg  1320
ccatctaatt taactgcttc ttctaatcct tctttggatt acggatttaa gggtgctgaa  1380
atagctatgg cttcatattg ttctgaattg cagtacttag ctaatcccgt tacttctcac  1440
gttcagtcag ctgaacagca caaccaagat gttaactctt tgggtttgat atcatctaga  1500
aaaacatcag aagctgttga tattttgaaa ttgatgtcta ctactttctt ggtcggtatt  1560
tgtcaagctg tcgacttgag gcatttggag gaaaatttga gacagacagt taaaaacact  1620
gtctcacaag ttgctaagaa agtcttgaca actggtatta atggtgaatt acatccatct  1680
aggttttgtg aaaaggactt gttaaaggtt gttgacagag aacaagtttt cacatacgtc  1740
gacgacccat gctcagctac ttacccattg atgcaaagat taagacaagt tatagttgat  1800
cacgctttat ctaatggtga gacagagaag aacgcagtta catctatttt tcaaaaaatt  1860
ggtgctttcg aagaagaatt gaaagcagtt ttgccaaagg aagttgaggc tgctagggct  1920
gcttacggaa atggtacagc tccaattcct aatagaatta aagaatgtcg ttcttaccca  1980
ttatacagat ttgtcagaga agaattaggt acaaagttat tgactggtga aaaggtcgtc  2040
tcacccggtg aggagtttga caaagttttt actgctatgt gtgagggtaa attaattgac  2100
cctttgatgg actgcttgaa agagtggaac ggtgctccta ttccaatttg ttaa        2154
```

```
SEQ ID NO: 2            moltype = DNA  length = 1518
FEATURE                 Location/Qualifiers
source                  1..1518
                        mol_type = other DNA
                        note = nucleotide sequence of C4H
                        organism = synthetic construct
SEQUENCE: 2
atggacttgt tgttgttgga aaagtcatta attgctgttt ttgttgctgt tattttggct  60
actgttattt ctaaattaag aggtaaaaag ttgaaattgc cacccggtcc aattcctatt  120
ccaatttttg gtaattggtt gcaagtcggt gacgatttga atcaccgtaa tttggttgat  180
tacgctaaaa agtttggtga cttattttta ttgagaatgg gtcaaagaaa tttagttgtt  240
gtttcttctc cagatttgac taaggaagtt ttattgacac aaggtgttga attcggttca  300
aggactagaa atgttgtttt cgatattttt actggtaaag gtcaagacat ggtttttaca  360
gtttatggtg aacactggag aaaaatgagg agaattatga ctgttccatt tttcacaaat  420
aaggtcgtcc agcagaatcg tgaaggatgg gagtttgaag ctgcatctgt cgtcgaagac  480
gtcaagaaga acccagattc tgctactaaa ggtattgttt tgaggaagag attgcaattg  540
atgatgtata ctaatatgtt taggataatg tttgatagaa gattcgaatc tgaagatgat  600
cctttgttct tgagattgaa ggctttgaat ggtgaaagat ctagattagc acaatctttt  660
gaatacaatt acggtgactt cataccaatt ttgagaccat ttttaagagg ttacttgaag  720
atttgccaag atgttaagga tagaagaatt gctttattta aaaagtactt cgttgatgaa  780
agaaaacaaa ttgcttcttc taagccaact ggttctgaag gtttaaaatg tgctattgac  840
catattttgg aagcagagca aaagggtgaa attaatgaag ataatgtttt gtacatagtt  900
gaaaatataa acgttgctgc tattgagact acattgtggt ctattgaatg gggtattgct  960
gaattagtca accaccccga aattcaatct aagttgggta acgaattgga cactgtcttg  1020
ggtcccggtg ttcaagtcac agagccagac ttgcataaat taccttattt gcaagcagtc  1080
gtcaaagaaa ctttaagatt gaggatggct attccattgt tggttcctca tatgaattta  1140
catgatgcta agttggctgg ttacgacata cccgctgagt ctaaaatttt ggttaatgca  1200
tggtggttgg ctaacaaccc aaactcttgg aagaagccag aggaatttcg tccagagagg  1260
ttcttcgaag aggagtctca cgttgaggct aacggtaacg actttcgtta cgtcccattc  1320
ggtgttggta ggagatcatg tcccggtatt atattagctt tgccaatttt gggtattact  1380
ataggtagaa tggtccaaaa ctttgagttg ttgccaccac ccggtcagtc taaggtcgac  1440
acttctgaga agggtggtca attttcatta catattttga accattctat tattgttatg  1500
aagccaagaa attgttaa                                                  1518
```

```
SEQ ID NO: 3            moltype = DNA  length = 1686
FEATURE                 Location/Qualifiers
source                  1..1686
                        mol_type = other DNA
                        note = nucleotide sequence of 4CL2
                        organism = synthetic construct
SEQUENCE: 3
atgattactg cagcattgca cgagccacag attcacaagc caactgacac ttctgtcgtc  60
tctgatgatg tcttgcctca ctctccacct actccaagga ttttcagatc aaaattgccc  120
gatattgata ttcctaatca cttaccattg catacatact gtttcgaaaa attgtcttca  180
gtctcagata agccatgttt gattgttggt tcaactggta aatcttacac ttacggtgaa  240
actcacttga tttgtcgtag ggtcgcttct ggtttgtaca agttgggaat aagaaaaggt  300
gatgttatta tgattttgtt acaaaattca gcagaattcg tcttctcatt tatgggtgct  360
tctatgattg gtgctgtttc tactacagct aacccatttt atacatctca agaattatat  420
```

```
aagcagttga aatcttctgg tgctaagttg ataattactc actctcagta cgttgataaa  480
ttgaagaatt taggtgaaaa tttgacattg attactactg atgaaccaac acccgaaaat  540
tgcttgccat tctctacttt gattactgac gatgagacta acccattcca agaaactgtc  600
gacattggtg gtgacgacgc agctgcatta ccattttctt ctggtactac tggtttacca  660
aaaggtgttg tcttgactca taagtcttta attacatctg tcgctcagca agttgatggt  720
gataacccaa acttatattt gaaatcaaat gatgttatat tatgtgtttt gccattattt  780
catatttact ctttgaattc agttttgtta aattcattga gatctggtgc tactgttttg  840
ttaatgcata agtttgaaat aggtgctttg ttggatttga ttcaaagaca tagagtcact  900
attgcagctt tggttccacc attggtcatt gctttggcta aaaaccctac agttaattct  960
tatgatttgt catctgtcag attcgtcttg tctggtgctg caccattggg aaaggagttg  1020
caagattctt tgaggaggag gttgccacaa gctattttgg gtcaaggtta cggtatgaca  1080
gaagctggtc cagtcttgtc tatgtctttg ggattcgcta aagaacctat tccaactaag  1140
tctggttctt gcggtacagt tgtcagaaac gctgagttga aggttgttca tttggaaaca  1200
aggttgtctt tgggttataa ccagcccggt gaaatatgta ttagaggaca acaaattatg  1260
aaggaatatt taaacgatcc agaagctact tctgctacta ttgacgagga gggttggttg  1320
catactggtg acattggtta cgtcgacgag gatgatgaaa tattcattgt tgatagatta  1380
aaagaagtta ttaaatttaa gggttttcaa gttccaccag ctgagttgga gtctttgtta  1440
attaatcatc actctattgc tgatgctgca gtcgttccac agaacgatga agttgctggt  1500
gaagtccccg ttgctttcgt cgttaggtct aatggtaacg atattacaga ggaagatgtt  1560
aaagaatacg tcgctaaaca agttgttttt tacaaaagat tgcataaagt tttcttcgtc  1620
gcatcaattc ctaaatctcc atctggtaaa attttgagaa aggatttaaa agctaagtta  1680
tgttaa                                                             1686
```

```
SEQ ID NO: 4           moltype = DNA  length = 1308
FEATURE                Location/Qualifiers
source                 1..1308
                       mol_type = other DNA
                       note = nucleotide sequence of HCT
                       organism = synthetic construct
SEQUENCE: 4
atgaaaattg aagttaaaga atctactatg gtcaagccag cagctgagac accacagcaa  60
agattgtgga actctaatgt tgatttggtt gtcccaaatt ttcatacacc atctgtttat  120
ttttacagac ctactggttc tccaaacttt tttgatggaa aagttttaaa ggaagcattg  180
tctaaagctt tggtcccttt ctacccaatg gctggtaggt tgtgcagaga cgaggatggt  240
agaattgaga ttgattgtaa gggtcaaggt gttttgttcg ttgaggcaga gtcagatggt  300
gttgtcgacg acttcggtga ctttgctcca acattggagt tgaggcagtt gattcccgct  360
gtcgactact ctcaaggtat tcaatcatac gctttattgg ttttgcaaat tactcacttt  420
aagtgcggtg gtgtctcttt gggtgttggt atgcagcatc atgcagctga tggtgcttct  480
ggtttgcact ttattaatac atggtctgat atggctagag gtttggattt aactattcca  540
ccttttattg atagaacatt gttaagagct agagacccac cacagccaca attccctcac  600
gtcgagtatc agccaccacc tactttgaag gtcactccag agaatacacc tatttctgaa  660
gctgttccag aaacatctgt ctctatattt aaattgacta gagatcaaat taacacattg  720
aaagcaaaat ctaaagaaga tggtaacaca gttaattact cttcttatga aatgttggct  780
ggacacgtct ggagatctac atgcatggct aggggtttgg ctcacgacca agaaactaaa  840
ttgtatattg ctacagacgg taggtctaga ttgaggccat ctttgccacc cggttacttt  900
ggtaacgtta tttttactac tactcctatt gctgttgctg gtgatattca atctaaacca  960
atttggtacg ctgcttctaa gttgcatgat gcattggcta gaatggataa tgactatttg  1020
agatctgcat tggattactt ggagttgcaa ccagacttga aggctttagt tcgtggtgct  1080
cacactttca agtgcccaaa cttgggtatt acttcttggt ctagattacc tattcatgat  1140
gctgatttcg gttggggtag gccaattttc atgggtcccg gtggtatagc ttacgaaggt  1200
ttatctttca ttttaccatc tccaactaat gatggttctc aatctgttgc tatttcttta  1260
caagctgaac atatgaaatt gtttgagaaa tttttgtacg atttttaa              1308
```

```
SEQ ID NO: 5           moltype = DNA  length = 720
FEATURE                Location/Qualifiers
source                 1..720
                       mol_type = other DNA
                       note = nucleotide sequence of CCoAoMT1
                       organism = synthetic construct
SEQUENCE: 5
atggctacta acggtagaca ccaagaagtt ggtcacaagt ctttgttgca gtctgatgca  60
ttgtatcaat atattttgga aacatctgtc tacccaagag agccagagcc tatgaaggag  120
ttgagagaaa ttacagctaa acatccatgg aatttgatga ctacttctgc tgatgaaggt  180
caatttttgt ctatgttgat taagttgatt aacgctaaaa atactatgga aattggtgtt  240
tttactggtt actcattgtt ggctacagct atggcattgc cagatgatgg taaaatatta  300
gctatggata ttaatagaga aaattatgaa attggtttgc cagttattga aaaagctggt  360
ttggctcata aaattgagtt taaagaaggt ccagctttgc cagtcttgga ccagatgata  420
gaagatggta aatatcacgg ttcttatgat tttattttcg ttgatgctga caaagataat  480
tatttaaact atcacaaaag attaattgat ttggttaaaa ttggtggttt gattggttat  540
gataacactt tgtggaatgg ttctgtcgtt gctccaccag atgcaccatt gagaaagtac  600
gttagatatt atagagattt tgttttagaa ttaaataaag cattggctgc tgattctaga  660
attgaaattt gccagttgcc agtcggtgac ggtataactt tgtgcagaag aatatcttaa  720
```

```
SEQ ID NO: 6           moltype = DNA  length = 834
FEATURE                Location/Qualifiers
source                 1..834
                       mol_type = other DNA
                       note = nucleotide sequence of FerB2
                       organism = synthetic construct
```

```
SEQUENCE: 6
atgtctgatg aattgacatt tgaaactgtt aaagttactt tggacgacgg tattgcttgg  60
gttgctttga acagaccaga gaagaggaac gctatgtctc caactgtcaa cagagagatg  120
tgggtcgcct tggacgagtt ggagattaga gacgacgtcg gtgtcgtcgt tttgactggt  180
gaaggtgagg ctttctctgc tggtatggac ttgaaggaat actttcgtga gactgagggt  240
gaatctgcta ttgtccaagc taggtatcgt agagctgcta ctgactggat gtggagaaga  300
ttgatgcatt acccaaagcc aactattgct atggtcaacg gttggtgctt cggtggtgct  360
ttcactccat tggtcgcttg tgacttggct attgctgcag acgaagctac tttcggtttg  420
tctgaaatta attggggtat tattccagct ggtaacgtta ctagagctgt cgctcaagtt  480
atgaatcata gagacgcttt gcactatatt atgactggtg atcctttcga cggtaaggaa  540
gctgctaaga tgggtttggt taatagatca gttccattag cagaattaag aggtgaagtt  600
gaagttttgg ctagaaaatt gttatctaaa aatccaacta ttttgagaca tgctaaatct  660
gcatttaaat atgtcgaaag attggactgg gacacttctg aagctatgtt gggtgctttg  720
gctgcaacag ctgcttctca agatactgag aggggtagaa ggaagggtat gacacaattt  780
ttggatgaaa agtcttttaa acccggtttg ggtggttata gaagagaaga ttaa        834

SEQ ID NO: 7           moltype = DNA  length = 1380
FEATURE                Location/Qualifiers
source                 1..1380
                       mol_type = other DNA
                       note = nucleotide sequence of pAMT
                       organism = synthetic construct
SEQUENCE: 7
atggcaaata ttacaaacga atttatgggt catgatatgt tagcaccatt cacagctggt  60
tggcagtcag acatggaacc attggttata gaaaagtctg aaggttctta cgtctatgat  120
attaacggta aaaagtactt ggatacattg tctggtttgt ggtgtgctac tttgggtggt  180
tctgagacaa gattggtcga agctgctaat aaacaattaa acactttacc attttaccac  240
tctttttgga acagaacaac aaaaccttct ttggatttag ctaaagagtt attgaatatg  300
tttactgcta ataaaatggc taaggtcttt tttacaaact ctggttctga agctaatgat  360
acacaagtca agatggtttg gtattataat aatgctttgg gtagacctca gaagaagaaa  420
attattgcta gagcaaaagc ttatcacggt tcaacataca tttctgctgg tttatctggt  480
ttgcctccaa tgcaccagaa gttcgacttg ccaccaccat tcgtcttgca tacagaatgc  540
ccacactact gggcatacca tttgcccggt gaaacagaag aagaattctc tactagattg  600
gcaaataatt tggaatcttt aattttgaaa gagggtccag aaactgtcgc tgcattcatt  660
gctgaaccag tcttgggtgc agctggtgtc attttaccac cagctactta ttttgataag  720
gttcaagcaa ttttgagaaa gcatgatatt ttgtttattg ctgatgaggt tgtttgcggt  780
ttcggtagat tgggaactat gtttggttct gataagtata acattaagcc agacttggtc  840
tcagtcggaa aggcattgtc ttctggttat atgccaattg ctgcagtttt agtttcacaa  900
aaaatttctt ctgtcatttt atctgaatct aataaaatag gtgctttttg tcatggtttc  960
acatactctg gtcatccagt tgcttgcgct gttgcattgg aggctttgaa aatttacaaa  1020
gaaaggaata ttacagaagt tgtcaataaa atttcacaga aattccaaga aggtttgaaa  1080
gcttttgctg attcaccaat tattggtgaa ataagaggta ctggtttggc tttgtctact  1140
gagttcgttg ataataaatc accaaatgat cctttcccat atgaatgggc tgtcggtact  1200
tacttcggtg ctcagtgcgc taagtacggt atgttggtct catctactgg tgaccacgtc  1260
aacatggctc caccatttat attgtctttg gaggaattgg atgagttaat tagaatatac  1320
ggtaaggctt taaaagatac agaaaaaaga gttgaagaat tgaagtcaca aaaacaataa  1380

SEQ ID NO: 8           moltype = DNA  length = 804
FEATURE                Location/Qualifiers
source                 1..804
                       mol_type = other DNA
                       note = nucleotide sequences of TDH3p
                       organism = synthetic construct
SEQUENCE: 8
atactagcgt tgaatgttag cgtcaacaac aagaagttta atgacgcgga ggccaaggca  60
aaaagattcc ttgattacgt aagggagtta gaatcatttt gaataaaaaa cacgcttttt  120
cagttcgagt ttatcattat caatactgcc atttcaaaga atacgtaaat aattaatagt  180
agtgattttc ctaactttat ttagtcaaaa aattagcctt ttaattctgc tgtaacccgt  240
acatgcccaa aatagggggc gggttacaca gaatatataa catcgtaggt gtctgggtga  300
acagtttatt cctggcatcc actaaatata atggagcccg ctttttaagc tggcatccag  360
aaaaaaaaag aatcccagca ccaaaatatt gttttcttca ccaaccatca gttcataggt  420
ccattctctt agcgcaacta cagagaacag gggcacaaac aggcaaaaaa cgggcacaac  480
ctcaatggag tgatgcaacc tgcctggagt aaatgatgac acaaggcaat tgacccacgc  540
atgtatctat ctcattttct tacaccttct attaccttct gctctctctg atttggaaaa  600
agctgaaaaa aaaggttgaa accagttccc tgaaattatt cccctacttg actaataagt  660
atataaagac ggtaggtatt gattgtaatt ctgtaaatct atttcttaaa cttcttaaat  720
tctactttta tagttagtct ttttttagt tttaaaacac caagaactta gtttcgaata  780
aacacacata aacaaacaaa gatg                                          804

SEQ ID NO: 9           moltype = DNA  length = 622
FEATURE                Location/Qualifiers
source                 1..622
                       mol_type = other DNA
                       note = nucleotide sequences of ADH1p
                       organism = synthetic construct
SEQUENCE: 9
acatgtaggt ggcggagggg agatatacaa tagaacagat accagacaag acataatggg  60
ctaaacaaga ctacaccaat tacactgcct cattgatggt ggtacataac gaactaatac  120
tgtagcccta gacttgatag ccatcatcat atcgaagttt cactaccctt tttccatttg  180
```

-continued

```
ccatctattg aagtaataat aggcgcatgc aacttctttt cttttttttt cttttctctc  240
tcccccgttg ttgtctcacc atatccgcaa tgacaaaaaa atgatggaag acactaaagg  300
aaaaaattaa cgacaaagac agcaccaaca gatgtcgttg ttccagagct gatgaggggt  360
atctcgaagc acacgaaact ttttccttcc ttcattcacg cacactactc tctaatgagc  420
aacggtatac ggccttcctt ccagttactt gaatttgaaa taaaaaaaag tttgctgtct  480
tgctatcaag tataaataga cctgcaatta ttaatctttt gtttcctcgt cattgttctc  540
gttccctttc ttccttgttt ctttttctgc acaatatttc aagctatacc aagcatacaa  600
tcaactatct catatacaga at                                             622

SEQ ID NO: 10          moltype = DNA  length = 750
FEATURE                Location/Qualifiers
source                 1..750
                       mol_type = other DNA
                       note = nucleotide sequences of PGK1p
                       organism = synthetic construct
SEQUENCE: 10
acgcacagat attataacat ctgcacaata ggcatttgca agaattactc gtgagtaagg  60
aaagagtgag gaactatcgc atacctgcat ttaaagatgc cgatttgggc gcgaatcctt  120
tattttggct tcaccctcat actattatca gggccagaaa aaggaagtgt ttccctcctt  180
cttgaattga tgttaccctc ataaagcacg tggcctctta tcgagaaaga aattaccgtc  240
gctcgtgatt tgtttgcaaa aagaacaaaa ctgaaaaaac ccagacacgc tcgacttcct  300
gtcttcctat tgattgcagc ttccaatttc gtcacacaac aaggtcctag cgacggctca  360
caggttttgt aacaagcaat cgaaggttct ggaatggcgg gaaagggttt agtaccacat  420
gctatgatgc ccactgtgat ctccagagca aagttcgttc gatcgtactg ttactctctc  480
tctttcaaac agaattgtcc gaatcgtgtg acaacaacag cctgttctca cacactcttt  540
tcttctaacc aagggggtgg tttagtttag tagaacctcg tgaaacttac atttacatat  600
atataaactt gcataaattg gtcaatgcaa gaaatacata tttggtcttt tctaattcgt  660
agtttttcaa gttcttagat gctttctttt tctctttttt acagatcatc aaggaagtaa  720
ttatctactt tttacaacaa atataaaaca                                     750

SEQ ID NO: 11          moltype = DNA  length = 562
FEATURE                Location/Qualifiers
source                 1..562
                       mol_type = other DNA
                       note = nucleotide sequences of TEF2p
                       organism = synthetic construct
SEQUENCE: 11
tatacttaca tatagtagat gtcaagcgta ggcgcttccc ctgccggctg tgagggcgcc  60
ataaccaagg tatctataga ccgccaatca gcaaactacc tccgtacatt catgttgcac  120
ccacacattt atacacccag accgcgacaa attacccata aggttgtttg tgacggcgtc  180
gtacaagaga acgtgggaac tttttaggct caccaaaaaa gaaagaaaaa atacgagttg  240
ctgacagaag cctcaagaaa aaaaaaattc ttcttcgact atgctggagg cagagatgat  300
cgagccggta gttaactata tatagctaaa ttggttccat caccttcttt tctggtgtcg  360
ctccttctag tgctatttct ggcttttcct attttttttt ttccattttt ctttctctct  420
ttctaatata taaattctct tgcattttct atttttctct ctatctattc tacttgttta  480
ttcccttcaa ggtttttttt taaggagtac ttgtttttag aatatacggt caacgaacta  540
taattaacta aacactagta cc                                             562

SEQ ID NO: 12          moltype = DNA  length = 405
FEATURE                Location/Qualifiers
source                 1..405
                       mol_type = other DNA
                       note = nucleotide sequences of TPI1t
                       organism = synthetic construct
SEQUENCE: 12
acctgattaa tataattata taaaaatatt atcttctttt ctttatatct agtgttatgt  60
aaaataaatt gatgactacg gaaagctttt ttatattgtt tctttttcat tctgagccac  120
ttaaatttcg tgaatgttct tgtaagggac ggtagattta caagtgatac aacaaaaagc  180
aaggcgcttt ttctaataaa aagaagaaaa gcatttaaca attgaacacc tctatatcaa  240
cgaagaatat tactttgtct ctaaatcctt gtaaaatgtg tacgatctct atatgggtta  300
ctcataagtg taccgaagac tgcattgaaa gtttatgttt tttcactgga ggcgtcattt  360
tcgcgttgag aagatgttct tatccaaatt tcaactgtta tatag                    405

SEQ ID NO: 13          moltype = DNA  length = 405
FEATURE                Location/Qualifiers
source                 1..405
                       mol_type = other DNA
                       note = nucleotide sequences of PGI1t
                       organism = synthetic construct
SEQUENCE: 13
atcgaacaaa tcgctcttaa atatatacct aaagaacatt aaagctatat tataagcaaa  60
gatacgtaaa ttttgcttat attattatac acatatcata tttctatatt tttaagattt  120
ggttatataa tgtacgtaat gcaaaggaaa taaattttat acattattga acagcgtcca  180
agtaactaca ttatgtgcac taatagttta gcgtcgtgaa gactttattg tgtcgcgaaa  240
agtaaaaatt ttaaaaatta gagcaccttg aacttgcgaa aaaggttctc atcaactgtt  300
taaaaggagg atatcaggtc ctatttctga caaacaatat acaaatttag tttcaaagat  360
gaatcagtgc gcgaaggaca taactcatga agcctccagt atacc                    405

SEQ ID NO: 14          moltype = DNA  length = 158
```

```
FEATURE                Location/Qualifiers
source                 1..158
                       mol_type = other DNA
                       note = nucleotide sequences of ADH1t
                       organism = synthetic construct
SEQUENCE: 14
agttataaaa aaaataagtg tatacaaatt ttaaagtgac tcttaggttt taaaacgaaa  60
attcttattc ttgagtaact ctttcctgta ggtcaggttg ctttctcagg tatagcatga  120
ggtcgctctt attgaccaca cctctaccgg catgccga                          158

SEQ ID NO: 15          moltype = DNA  length = 248
FEATURE                Location/Qualifiers
source                 1..248
                       mol_type = other DNA
                       note = nucleotide sequences of CYC1t
                       organism = synthetic construct
SEQUENCE: 15
tcatgtaatt agttatgtca cgcttacatt cacgccctcc ccccacatcc gctctaaccg  60
aaaaggaagg agttagacaa cctgaagtct aggtccctat ttattttttt atagttatgt  120
tagtattaag aacgttattt atatttcaaa tttttctttt ttttctgtac agacgcgtgt  180
acgcatgtaa cattatactg aaaaccttgc ttgagaaggt tttgggacgc tcgaaggctt  240
taatttgc                                                           248

SEQ ID NO: 16          moltype = DNA  length = 520
FEATURE                Location/Qualifiers
source                 1..520
                       mol_type = other DNA
                       note = nucleotide sequences of ENO2p
                       organism = synthetic construct
SEQUENCE: 16
acgcggcgtt atgtcactaa cgacgtgcac caacttgcgg aaagtggaat cccgttccaa  60
aactggcatc cactaattga tacatctaca caccgcacgc ctttttttctg aagcccactt  120
tcgtggactt tgccatatgc aaaattcatg aagtgtgata ccaagtcagc atacacctca  180
ctagggtagt ttctttggtt gtattgatca tttggttcat cgtggttcat taattttttt  240
tctccattgc tttctggctt tgatcttact atcatttgga tttttgtcga aggttgtaga  300
attgtatgtg acaagtggca ccaagcatat ataaaaaaaa aaagcattat cttcctacca  360
gagttgattg ttaaaaacgt atttatagca aacgcaattg taattaattc ttattttgta  420
tcttttcttc ccttgtctca atcttttatt tttattttat ttttcttttc ttagtttctt  480
tcataacacc aagcaactaa tactataaca tacaataata                        520

SEQ ID NO: 17          moltype = DNA  length = 290
FEATURE                Location/Qualifiers
source                 1..290
                       mol_type = other DNA
                       note = nucleotide sequences of PYK1p
                       organism = synthetic construct
SEQUENCE: 17
aggagacgtt actttgttta tatatattag tatgtacaat cgcaaagaaa tggagtgatg  60
acatgttgta gtatttagta tgaggttact gtgtgggagg ttttaccatg atttttggcg  120
agaacacgcc atgaaatgtc tttgtacgaa actcattacc cgcattaata tttttttttct  180
ttttaaagct cagttgaccc tttctcattc ccttcttaaa acaactgtgt gatccttgag  240
aaaagataaa ttacatacac aacataaacc caactacgat cgcaaattat             290

SEQ ID NO: 18          moltype = DNA  length = 630
FEATURE                Location/Qualifiers
source                 1..630
                       mol_type = other DNA
                       note = nucleotide sequences of FBA1p
                       organism = synthetic construct
SEQUENCE: 18
ataacaatac tgacagtact aaataattgc ctacttggct tcacatacgt tgcatacgtc  60
gatatagata ataatgataa tgacagcagg attatcgtaa tacgtaatag ttgaaaatct  120
caaaaatgtg tgggtcatta cgtaaataat gataggaatg ggattcttct atttttcctt  180
tttccattct agcagccgtc gggaaaacgt ggcatcctct ctttcgggct caattggagt  240
cacgctgccg tgagcatcct ctctttccat atctaacaac tgagcacgta accaatggaa  300
aagcatgagc ttagcgttgc tccaaaaaag tattggatgg ttaataccat ttgtctgttc  360
tcttctgact ttgactcctc aaaaaaaaaa aatctacaat caacagatcg cttcaattac  420
gccctcacaa aaactttttt ccttcttctt cgcccacgtt aaattttatc cctcatgttg  480
tctaacggat ttctgcactt gatttattat aaaaagacaa agacataata cttctctatc  540
aatttcagtt attgttcttc cttgcgttat tcttctgttc ttcttttttct tttgtcatat  600
ataaccataa ccaagtaata catattcaaa                                   630

SEQ ID NO: 19          moltype = DNA  length = 469
FEATURE                Location/Qualifiers
source                 1..469
                       mol_type = other DNA
                       note = nucleotide sequences of HOG1t
                       organism = synthetic construct
SEQUENCE: 19
```

```
tttaatgtcc ctaaccactc attcttactt ctttttgatg tttctttttt ttatggtact  60
cataaaagta tttacgtata tagttgtata gaggaaacaa aaaaaaaaag ataaaactca  120
attacaaagt aaagtggacg tatttcgatc atgatttttt tctgttttaa ccgcattgga  180
ttttcttgta aaactggaag aaaaaggaaa ctaaaaagtc aagaaagacc tttttaagac  240
tccaagaacc gtcacttatg gcgtattgtt tgtttatcag cacttctatc ttcgataaag  300
gtttgtctgt cttatattgt ttacatttca agtctaattc tgtgctttta ccgaagagga  360
attttcataa atacggagaa aatataaaaa aaaagtaaat acagaaaata gaacagttga  420
agcagaaaaa gagaacttgc taaatagctg tctcacccag acaagcgta             469
```

```
SEQ ID NO: 20          moltype = DNA  length = 438
FEATURE                Location/Qualifiers
source                 1..438
                       mol_type = other DNA
                       note = ucleotide sequences of LRP1t
                       organism = synthetic construct
SEQUENCE: 20
aggtcgacgt atactggtac atgagtgaaa aaatgattaa aggtgatgtg agagcacaaa  60
tgcaaaaatg cttatagggt ttatatactt ttataataac aataagaact cgttgaagta  120
actaatatgt gtatatgcta ttcttgtagt tggcagtgaa cacttttgtg tgaattgacg  180
ttatataaga ctgtagaaat atctaagaaa agagagtttt cataaaaccc ttcaagctta  240
actaccaaaa agcattcata cttagaagtt gaaatgcacg atgatgccaa attgatgaaa  300
aaagctaaaa atgcatttca gaagggaaga aaataataag caacataaca gagggaatag  360
gtgcgcttag tcttgttgct gtaaaattaa ccaattattc ttgtattgtt ctaacgatcc  420
gaccatttca tcctgaat                                                438
```

```
SEQ ID NO: 21          moltype = DNA  length = 458
FEATURE                Location/Qualifiers
source                 1..458
                       mol_type = other DNA
                       note = nucleotide sequences of ATP15t
                       organism = synthetic construct
SEQUENCE: 21
tttaacgctt cctgggaact gcagctcttt ttttactcgc tgatatacat tttaaatatt  60
ctagcaactg tgtatgaaaa cttacgtact tttatacggg aaactaataa tgactacaat  120
gatattgaat actggccgct tcgaagagtg gtataaagtt tgtatcattg cattaaaaga  180
aaaagaaata tatgtcccat catcgccaat cgcaatgttg aatggtcgtt taccactttt  240
gcggctgggc atatgcagaa acatgctgtc ccgtccccga ctggctaaac tgccatctat  300
aaggtttcgg tctttggtca ccccttcttc atcgcagctc attcctctca gtcggttgtg  360
tttaaggtca cctgcagttg gaaaatcact aattttacaa agttttagat gtaattcatc  420
caaaacagtt ccagaaactt ctctgccttc agcctctc                          458
```

```
SEQ ID NO: 22          moltype = DNA  length = 1161
FEATURE                Location/Qualifiers
source                 1..1161
                       mol_type = other DNA
                       note = nucleotide sequence of coding gene pheA
                       organism = synthetic construct
SEQUENCE: 22
atgacatcgg aaaacccgtt actggcgctg cgagagaaaa tcagcgcgct ggatgaaaaa  60
ttattagcgt tactggcaga acggcgcgaa ctggccgtcg aggtgggaaa agccaaactg  120
ctctcgcatc gcccggtacg tgatattgat cgtgaacgcg atttgctgga aagattaatt  180
acgctcggta aagcgcacca tctggacgcc cattacatta ctcgcctgtt ccagctcatc  240
attgaagatt ccgtattaac tcagcaggct ttgctccaac aacatctcaa taaaattaat  300
ccgcactcag cacgcatcgc ttttctcggc cccaaaggtt cttattccca tcttgcggcg  360
cgccagtatg ctgcccgtca ctttgagcaa ttcattgaaa gtggctgcgc caaatttgcc  420
gatattttta atcaggtgga aaccggccag gccgactatg ccgtcgtacc gattgaaaat  480
accagctccg gtgccataaa cgacgtttac gatctgctgc aacataccag cttgtcgatt  540
gttggcgaga tgacgttaac tatcgaccat tgtttgttgg tctccggcac tactgattta  600
tccaccatca atacggtcta cagccatccg cagccattcc agcaatgcag caaattcctt  660
aatcgttatc cgcactggaa gattgaatat accgaaagta cgtctgcggc aatggaaaag  720
gttgcacagg caaaatcacc gcatgttgct gcgttgggaa gcgaagctgg cggcactttg  780
tacggtttgc aggtactgga gcgtattgaa gcaaatcagc gacaaaactt cacccgattt  840
gtggtgttgg cgcgtaaagc cattaacgtg tctgatcagg ttccggcgaa aaccacgttg  900
ttaatggcga ccgggcaaca agccggtgcg ctggttgaag cgttgctggt actgcgcaac  960
cacaatctga ttatgacccg tctggaatca cgcccgattc acggtaatcc atgggaagag  1020
atgttctatc tggatattca ggccaatctt gaatcagcgg aaatgcaaaa agcattgaaa  1080
gagttagggg aaatcacccg ttcaatgaag gtattgggct gttacccaag tgagaacgta  1140
gtgcctgttg atccaacctg a                                            1161
```

```
SEQ ID NO: 23          moltype = DNA  length = 1542
FEATURE                Location/Qualifiers
source                 1..1542
                       mol_type = other DNA
                       note = nucleotide sequence of transaminase coding gene Aro9
                       organism = synthetic construct
SEQUENCE: 23
atgactgctg gttctgcccc ccctgttgat tacacttcct taaagaagaa cttccaaccg  60
tttctctcca gaagagtaga aaatagatct ctgaaaagct tttgggatgc ttctgatatc  120
tcagatgacg tcattgagct agctggtgga atgccaaacg agagattttt tcctatcgaa  180
```

```
tctatggatt tgaaaatatc aaaagttcct tttaatgata acccaaaatg gcataattcg  240
tttaccacgg cgcatttgga cttgggatcc cccagtgagc tacccattgc acgttctttc  300
caatatgcag aaaccaaggg tttaccccct ctcttacatt ttgttaaaga ttttgtgtcc  360
agaattaatc gcccagcctt ttccgatgag acggagtcta actgggatgt catcctttct  420
ggcgggtcca acgattcaat gtttaaggtt tttgaaacaa tttgcgacga atcgaccact  480
gtgatgattg aagagtttac tttcaccccg gctatgtcca atgtggaggc tacaggagca  540
aaagtcatcc ccatcaagat gaacctgacc ttcgacagag agtcccaggg tattgatgtc  600
gaatatctaa cgcagttgct cgataattgg tcaactggac catacaaaga cttaaacaag  660
ccaagggtcc tatataccat tgcaacgggc caaaatccta ccgggatgtc tgtcccccag  720
tggaaaagag agaaaattta ccagttggcc caaagacacg atttcctcat tgttgaagat  780
gatccctacg gttatctgta ctttccttcc tataatccgc aagagccatt agaaaaccct  840
taccattcta gcgacctgac tactgaacgg tatttgaatg attttttaat gaaatcattc  900
ttgactttgg atacagatgc ccgtgtcatc cgtttggaga ctttttctaa aatttttgct  960
cctggattaa ggttatcctt catcgttgct aataaattcc ttttgcaaaa aatcttggat  1020
ttggccgaca ttactacaag ggcccccagt ggtacctcac aagctattgt ttattctaca  1080
ataaaggcaa tggctgagtc caacttatcg tcctctcttt ctatgaaaga agcaatgttt  1140
gagggttgga taagatggat aatgcagatt gcttctaaat acaatcatag gaaaaatctt  1200
actttgaaag ccttatacga aacagaatct taccaagctg gtcagtttac cgttatggaa  1260
ccctccgcgg gtatgttcat cattattaaa atcaattggg ggaatttcga tagacctgac  1320
gatttgccgc aacagatgga tattttagat aagttcttgc tgaagaatgg tgttaaagta  1380
gtgcttggtt ataaaatggc tgtttgccca aattattcaa agcagaattc agattttcta  1440
agactcacca tcgcctatgc aagggatgat gatcagttga ttgaagcttc caaaagaatc  1500
ggtagtggca taaaagaatt ttttgacaac tataaaagtt ga                     1542

SEQ ID NO: 24          moltype = DNA  length = 290
FEATURE                Location/Qualifiers
source                 1..290
                       mol_type = other DNA
                       note = nucleotide sequence of PFY1p promoter
                       organism = synthetic construct
SEQUENCE: 24
aggagacgtt actttgttta tatatattag tatgtacaat cgcaaagaaa tggagtgatg  60
acatgttgta gtatttagta tgaggttact gtgtgggagg ttttaccatg atttttggcg  120
agaacacgcc atgaaatgtc tttgtacgaa actcattacc cgcattaata ttttttttct  180
ttttaaagct cagttgaccc tttctcattc ccttcttaaa acaactgtgt gatccttgag  240
aaaagataaa ttacatacac aacataaacc caactacgat cgcaaattat             290

SEQ ID NO: 25          moltype = DNA  length = 669
FEATURE                Location/Qualifiers
source                 1..669
                       mol_type = other DNA
                       note = nucleotide sequence of ACT1p promoter
                       organism = synthetic construct
SEQUENCE: 25
acaagcgcgc ctctaccttg cagacccata taatataata actaaataag taaataagac  60
acacgcgaga acatatatac acaattacag taacaataac aagaggacag atactaccaa  120
aatgtgtggg gaagcgggta agctgccaca gcaattaatg cacaacattt aacctacatt  180
cttccttatc ggatcctcaa aacccttaaa aacatatgcc tcaccctaac atattttcca  240
attaaccctc aatatttctc tgtcacccgg cctctatttt ccattttctt ctttacccgc  300
cacgcgtttt tttctttcaa attttttttct tccttcttct ttttcttcca cgtcctcttg  360
cataaataaa taaaccgttt tgaaaccaaa ctcgcctctc tctctccttt ttgaaatatt  420
tttgggtttg tttgatcctt tccttcccaa tctctcttgt ttaatatata ttcatttata  480
tcacgctctc tttttatctt ccttttttttc ctctctcttg tattcttcct tccccttttct  540
actcaaacca agaagaaaaa gaaaaggtca atctttgtta aagaatagga tcttctacta  600
catcagcttt tagatttttc acgcttactg cttttttctt cccaagatcg aaaatttact  660
gaattaaca                                                          669

SEQ ID NO: 26          moltype = DNA  length = 408
FEATURE                Location/Qualifiers
source                 1..408
                       mol_type = other DNA
                       note = nucleotide sequence of PRC1t terminator
                       organism = synthetic construct
SEQUENCE: 26
taaagcgtgt atgtgtaggc ataccgtttt tattatcagc tacgatcgaa atatatacgt  60
ttttatctat gttacgttat atattgtagt cttaaccatt tgtaagtttt gcttcttttc  120
ttttattcat ttcataacat catactgttt tacgtaatac catccttaac tttttccacc  180
gaaggggagg aagaactaaa ttctagaaaa atgaaaccat taaaaaaaaa gaaaacaata  240
gagctgcttc tacaattttg cacatcaaaa aagacctcca actaccgagt ttgtaagtac  300
aatgtctcaa cccactccca tcataactac aaaatcagct gctaagccaa aaccaaaaat  360
ttttaattta ttccgcgttt gcttcatttc attattgctg atcgctgc               408

SEQ ID NO: 27          moltype = DNA  length = 416
FEATURE                Location/Qualifiers
source                 1..416
                       mol_type = other DNA
                       note = nucleotide sequence of BAN4t terminator
                       organism = synthetic construct
SEQUENCE: 27
```

```
agccagttta ttcttgccat ccgtgtacgc taggagagga ttattaaaat aagtgatata  60
tacatatata tatatatata tatatatata atacactaat tattttatgt gatgttgatc  120
acgcgaaacg gtaaacggct ctgttcgcgc tttctttgtt tacattttag tgaagtattg  180
tcaagataat atccatatgg ttgaactttt tatattggct agttaaatac tctatttatt  240
gcaccaaaaa atcatcttag tggacttttt ggagcaaaaa aaaccagcag gtagttatat  300
aagatgacta cacaactaag gtatgaaaat aacgatgacg atgaaagagt agaatataat  360
ctctttacca atagatccac catgatggca aattttgaag aatggatcaa aatggc      416

SEQ ID NO: 28          moltype = DNA  length = 1533
FEATURE                Location/Qualifiers
source                 1..1533
                       mol_type = other DNA
                       note = nucleotide sequence coding gene TAL
                       organism = synthetic construct
SEQUENCE: 28
atgactcaag ttgttgaaag acaagctgac agattgtctt ctagagaata cttggctaga  60
gttgttagat ctgctggttg ggacgctggt ttgacttctt gtactgacga agaaatcgtt  120
agaatgggtg cttctgctag aactatcgaa gaatacttga agtctgacaa gccaatctac  180
ggtttgactc aaggtttcgg tccattggtt ttgttcgacg ctgactctga attggaacaa  240
ggcggcagct tgatctctca cctcggtact ggtcaaggtg ctccattggc tccagaagtt  300
tctagattga tcttgtggtt gagaatccaa aacatgagaa agggttactc tgctgtttct  360
ccagttttct ggcaaaagtt ggctgacctc tggaacaagg gcttcactcc agctatacca  420
agacacggta ctgtttctgc ttctggtgac ttgcaaccat tggctcacgc tgctttggct  480
ttcactggtg ttggtgaagc ttggactaga gacgctgacg gtagatggtc tactgttcca  540
gctgttgacg ctttggctgc tttgggtgct gaaccattcg actggccagt tagagaagct  600
ttggctttcg ttaacggtac tggtgcttct ttggctgttg ctgttttgaa ccacagatct  660
gctttgagat tggttagagc ttgtgctgtt ttgtctgcta gactcgcgac attgttgggt  720
gctaatccag aacactacga cgttggtcac ggtgttgcta gaggtcaagt tggtcaattg  780
actgctgctg aatggatcag acaaggtttg ccaagaggta tggttagaga cggttctaga  840
ccattgcaag aaccatactc tttgagatgt gctccacaag ttttgggtgc tgttttggac  900
caattggacg gtgctggtga cgttttggct agagaagttg acggttgtca agacaaccca  960
atcacttacg aaggtgaatt gttgcacggt ggtaacttcc acgctatgcc agttggtttc  1020
gcttctgacc aaatcggttt ggctatgcac atggctgctt acttggctga aagacaattg  1080
ggtttgttgg tttctccagt tactaacggt gacttgccac caatgttgac tccaagagct  1140
ggtagaggtg ctggtttggc tggtgttcaa atctctgcta cttctttcgt ttctagaatc  1200
agacaattgg ttttcccagc ttctttgact actttgccaa ctaacggttg gaaccaagac  1260
cacgttccaa tggctttgaa cggtgctaac tctgttttcg aagctttgga attgggttgg  1320
ttgactgttg gttctttggc tgttggtgtt gctcaattgg ctgctatgac tggtcacgct  1380
gctgaaggtg tttgggctga attggctggt atctgtccac cattggacgc tgacagacca  1440
ttgggtgctg aagttagagc tgctagagac ttgttgtctg ctcacgctga ccaattgttg  1500
gttgacgaag ctgacggtaa ggacttcggt taa                               1533

SEQ ID NO: 29          moltype = DNA  length = 398
FEATURE                Location/Qualifiers
source                 1..398
                       mol_type = other DNA
                       note = nucleotide sequence of promoter HXT7p
                       organism = synthetic construct
SEQUENCE: 29
actacttctc gtaggaacaa tttcgggccc ctgcgtgttc ttctgaggtt catcttttac  60
atttgcttct gctggataat tttcagaggc aacaaggaaa aattagatgg caaaaagtcg  120
tctttcaagg aaaaatcccc accatctttc gagatcccct gtaacttatt ggcaactgaa  180
agaatgaaaa ggaggaaaat acaaaatata ctagaactga aaaaaaaaaa gtataaatag  240
agacgatata tgccaatact tcacaatgtt cgaatctatt cttcatttgc agctattgta  300
aaataataaa acatcaagaa caaacaagct caacttgtct tttctaagaa caaagaataa  360
acacaaaaac aaaaagtttt tttaatttta atcaaaaa                          398

SEQ ID NO: 30          moltype = DNA  length = 499
FEATURE                Location/Qualifiers
source                 1..499
                       mol_type = other DNA
                       note = nucleotide sequence of terminator PRS28At
                       organism = synthetic construct
SEQUENCE: 30
gaagcttatt tgcagattga aggttgcagc tatacaaaat ctatcttata tatttgtgcc  60
ttttgtttct tatatatgtc ttctttaaat agtacatcac tataatacaa taatactaat  120
aactctattg taactcgtga tatattcact aattatttag gtgcgaaaaa ccatacccgc  180
attgatatac tttttgggta tattgagttc ttccgcgtta gttgttatgg gccttctatg  240
gtagacaaga attttatata cgtaggccta acattagtgg ctccagctgc ttaccaaatc  300
catgaccgat gagaaacgag cttttccaaa aggtaacaac catataagat cagaaacttt  360
caatggttcg gtatctcaca aaatctccga atcgattaaa gatatcgcta gcttaagacc  420
acacggtaaa tatacggtac aagacatcga caacatcata gcatccacat cttcacatga  480
aaatagaggc caatcaggc                                               499

SEQ ID NO: 31          moltype = DNA  length = 1350
FEATURE                Location/Qualifiers
source                 1..1350
                       mol_type = other DNA
                       note = nucleotide sequence of coding gene sahH of SAH
```

```
                          hydrolase
                         organism = synthetic construct
SEQUENCE: 31
atgtctgctc cagctcaaaa ctacaaaatc gctgatatct ctttggctgc cttcggtaga  60
aaggaaatcg aattggctga acatgaaatg ccaggtttga tggccatcag aaaggcttac  120
ggtgacgtcc aacctttgaa aggcgcccgt attgctggtt gtttgcacat gaccattcaa  180
actgctgttt taattgaaac tttagttgct ttgggtgccg aagttacctg gtcctcttgt  240
aacatctatt cgactcaaga tcatgccgcc gctgctattg ccgcttccgg tgttccagtt  300
tttgcctgga agggtgaaac tgaagaagag tatttgtggt gtattgaaca acaattgttt  360
gccttcaagg acaacaagaa attgaacttg atcttagatg atggtggtga tttaaccact  420
ttagttcatg aaaagcaccc tgaaatgctg gaagactgct ttggtctttc cgaagaaact  480
accaccggtg ttcaccactt atacagaatg gtcaaagaag gcaagttaaa ggttcctgcc  540
attaacgtta acgactccgt cactaagtcc aagtttgaca acttgtacgg ctgtagagaa  600
tccttagtcg acggtattaa gagagccact gatgtcatgt tggctggtaa ggttgccgtt  660
gttgctggtt acggtgatgt cggtaagggt tgtgctgctg ccttaagagg aatgggtgct  720
cgtgtcttgg ttaccgaaat tgacccaatc aacgctttac aagctgccat ggaaggctac  780
caagttgtta ccatggaaga tgcatcccac attggtcaag ttttcgttac caccactggt  840
tgtagagata ttatcaacgg tgaacatttc atcaacatgc cagaagatgc cattgtttgt  900
aacattggcc atttcgatat cgaaattgat gtcgcctggt taaaggctaa cgctaaagaa  960
tgtattaaca tcaaaccaca agtcgaccgt tacttgttgt cttctggtag acacgtcatc  1020
ttgttggcta acggtagatt agttaacttg ggttgtgcta ctggtcactc atctttcgtt  1080
atgtcttgtt ccttctctaa ccaagtctta gctcaaattg ctttgttcaa gtctaacgat  1140
aagtctttca gagaaaagca cattgaattc caaaagacag gcccattcga agttggtgtc  1200
cacgttttgc caaagatctt ggatgaagct gtcgctaagt tccacttggg caacttgggt  1260
gttagattga ctaaattgag taaagtccaa tctgaatact tgggtattcc agaagaaggt  1320
ccattcaagg ccgaccacta cagatattga                                 1350

SEQ ID NO: 32            moltype = DNA  length = 1182
FEATURE                  Location/Qualifiers
source                   1..1182
                         mol_type = other DNA
                         note = nucleotide sequence of gene SAM2
                         organism = synthetic construct
SEQUENCE: 32
atggaaactt tcttgttcac ttctgaatct gttaacgaag gtcacccaga caagttgtgt  60
gaccaaatct ctgacgctgt tttggacgct tgtttggaac aagacccaga ctctaaggtt  120
gcttgtgaaa cttgtactaa gactaacatg gttatggttt tcggtgaaat cactactaag  180
gctactatcg actacgaaaa gatcgttaga gacacttgta gatctatcgg tttcatctct  240
gacgacgttg gtttggacgc tgacaagtgt aaggttttgg ttaacatcga acaacaatct  300
ccagacatcg ctcaaggtgt tcacggtcac ttcactaaga gaccagaaga catcggtgct  360
ggtgaccaag gtcacatgtt cggttacgct actgacgaaa ctccagaatt gatgccattg  420
tctcacgttt tggctactaa gatcggtgct agattgactg aagttagaaa gaacggtact  480
tgtagatggt tgagaccaga cggtaagact caagttactg ttgaatacta caacgacaac  540
ggtgctatgg ttccagttag agttcacact gttttgatct ctactcaaca cgacgaaact  600
gttactaacg acgaaatcgc tagagacttg aaggaacacg ttatcaagcc aatcatccca  660
gaaaagtact tggacgacaa gactatcttc cacttgaacc catctggtag attcgttatc  720
ggtggtccac acggcgacgc tggtctcact ggtagaaaga tcatcatcga cacttacggt  780
ggttggggtg ctcacggtgg tggtgctttc tctggtaagg acccaactaa ggttgacaga  840
tctggtgctt acatcgttag acaagctgct aagtctgttg ttgctaacgg tatggctaga  900
agagctttgg ttcaagtttc ttacgctatc ggtgttccag aaccattgtc tgttttcgtt  960
gacacttacg gtactggttt gatcccagac aaggaaatct tgaagatcgt taaggaaact  1020
ttcgacttca gaccaggtat gatgactatc aacttggact tgaagagagg tggtaacggt  1080
agattccaaa agactgctgc ttacggtcac ttcggtagag acgacccaga cttcacttgg  1140
gaagttgtta agccattgaa gtgggacaag ccacaagctt aa                   1182

SEQ ID NO: 33            moltype = DNA  length = 500
FEATURE                  Location/Qualifiers
source                   1..500
                         mol_type = other DNA
                         note = nucleotide sequence of promoter CYC1p
                         organism = synthetic construct
SEQUENCE: 33
aatttttttg gaaaaccaag aaatgaatta tatttccgtg tgagacgaca tcgtcgaata  60
tgattcaggg taacagtatt gatgtaatca atttcctacc tgaatctaaa attcccggga  120
gcaagatcaa gatgttttca ccgatctttc cggtctcttt ggccggggtt tacggacgat  180
ggcagaagac caaagcgcca gttcatttgg cgagcgttgg ttggtggatc aagcccacgc  240
gtaggcaatc ctcgagcaga tccgccaggc gtgtatatat agcgtggatg gccaggcaac  300
tttagtgctg acacatacag gcatatatat atgtgtgcga cgacacatga tcatatggca  360
tgcatgtgct ctgtatgtat ataaaactct tgttttcttc ttttctctaa atattctttc  420
cttatacatt aggacctttg cagcataaat tactatactt ctatagacac acaaacacaa  480
atacacacac taaattaata                                            500

SEQ ID NO: 34            moltype = DNA  length = 433
FEATURE                  Location/Qualifiers
source                   1..433
                         mol_type = other DNA
                         note = nucleotide sequence of terminator ALY2t
                         organism = synthetic construct
SEQUENCE: 34
```

```
tctagcacaa ggttcctacg tcatcccttc ctgttcttac atctggcgtc cagagcaaac  60
ataaaatatt agaaactcta attgttatac atatatatgt ttatatctgt ttatggtacg  120
ttcttttctt taattttgct tttgaaaag tgatgttcgc aatctatctc actaattggt  180
taagaacagt agttagttcg tcaggggtat atttgatatg ctttctagga ttcttgaaag  240
agtctttata tctactgtag aatctttcat acatgggcat aaccaacgat attatttctg  300
acttcaaagt tactttcaat gatggatctg aaagcttata ctgttttgtt tttgatacta  360
aatcttcgaa tccttcattg aattttctaa atttctcctt tatttgttct ttgtcttttg  420
acttcttccc gct                                                    433

SEQ ID NO: 35          moltype = DNA  length = 402
FEATURE                Location/Qualifiers
source                 1..402
                       mol_type = other DNA
                       note = nucleotide sequence of terminator SCW4t
                       organism = synthetic construct
SEQUENCE: 35
gtctactcaa ttgtaaaaaa aaacaaaaaa aatcttgatt taaaaaacga tacccaatat  60
ttttaacttt aaattaaggc tttgataatc ttctttttct ctgttatatc aaaggactgc  120
tttctggttt gccttcgcta atcttttttt ttttttttca ttttcctatt ttagttcgtt  180
tatgatctca tttgtatttc tgtatatttg tcttaatacg aaatacgagt ttttatttta  240
tattctacct ttcttttttt tttggctaaa agcgtgtacg gttctatgta aatatgtacg  300
attacatgtg taatgtttgt ttggccgggc tcttcatcta tgccgttgcc ttcttgcagg  360
cggagtcctg gatctgttac gatggtttct cgatcctctt gg                     402

SEQ ID NO: 36          moltype = DNA  length = 699
FEATURE                Location/Qualifiers
source                 1..699
                       mol_type = other DNA
                       note = nucleotide sequence of mtn
                       organism = synthetic construct
SEQUENCE: 36
atgaaaatcg gcatcattgg tgcaatggaa gaagaagtta cgctgctgcg tgacaaaatc  60
gaaaaccgtc aaactatcag tctcggcggt tgcgaaatct ataccggcca actgaatgga  120
accgaggttg cgcttctgaa atcgggcatc ggtaaagtcg ctgcggcgct gggtgccact  180
ttgctgttgg aacactgcaa gccagatgtg attattaaca ccggttctgc cggtggcctg  240
gcaccaacgt tgaaagtggg cgatatcgtt gtctcggacg aagcacgtta tcacgacgcg  300
gatgtcacgg catttggtta tgaatacggt cagttaccag gctgtccggc aggctttaaa  360
gctgacgata aactgatcgc tgccgctgag gcctgcattg ccgaactgaa tcttaacgct  420
gtacgtggcc tgattgttag cggcgacgct ttcatcaacg gttctgttgg tctggcgaaa  480
atccgccaca acttcccaca ggccattgct gtagagatgg aagcgacggc aatcgcccat  540
gtctgccaca atttcaacgt cccgtttgtt gtcgtacgcg ccatctccga cgtggccgat  600
caacagtctc atcttagctt cgatgagttc ctggctgttg ccgctaaaca gtccagcctg  660
atggttgagt cactggtgca gaaacttgca catggctaa                         699

SEQ ID NO: 37          moltype = DNA  length = 516
FEATURE                Location/Qualifiers
source                 1..516
                       mol_type = other DNA
                       note = nucleotide sequence of luxS
                       organism = synthetic construct
SEQUENCE: 37
atgccgttgt tagatagctt cacagtcgat catacccgga tggaagcgcc tgcagttcgg  60
gtggcgaaaa caatgaacac cccgcatggc gacgcaatca ccgtgttcga tctgcgcttc  120
tgcgtgccga acaaagaagt gatgccagaa agagggatcc ataccctgga gcacctgttt  180
gctggtttta tgcgtaacca tcttaacggt aatggtgtag agattatcga tatctcgcca  240
atgggctgcc gcaccggttt ttatatgagt ctgattggta cgccagatga gcagcgtgtt  300
gctgatgcct ggaaagcggc aatggaagac gtgctgaaag tgcaggatca gaatcagatc  360
ccggaactga acgtctacca gtgtggcact taccagatgc actcgttgca ggaagcgcag  420
gatattgcgc gtagcattct ggaacgtgac gtacgcatca acagcaacga agaactggca  480
ctgccgaaag agaagttgca ggaactgcac atctag                            516

SEQ ID NO: 38          moltype = DNA  length = 423
FEATURE                Location/Qualifiers
source                 1..423
                       mol_type = other DNA
                       note = nucleotide sequence of terminator NAT5t
                       organism = synthetic construct
SEQUENCE: 38
atttcttaac agatggctga aaaatttttt tttttttttt ggttttgctt tgtatacaca  60
tgtatctatt tttataaaga tgaaatatat acgtctaaga gctaaaatga aaaactatac  120
taatcactta tatctattct ggtgattcat catcttcagc ttctgtatcc gtatcgatat  180
cagtataatc gctagcatca ctttcatcat cactttcggt ttcgtcgtca tcagtagagt  240
actcatcatc ctcctcagaa tacacctcta cttgttccac tgcaggagaa tcacgaactt  300
tcatattcat ggtaatatcc aaatctgtag tgaaataatc tgtggattta acgattactc  360
taaaaaagaa atcaccaaca gtttcaggtg caggctgacc taatggaatt tttatggtcc  420
cga                                                               423

SEQ ID NO: 39          moltype = DNA  length = 462
FEATURE                Location/Qualifiers
```

```
source                  1..462
                        mol_type = other DNA
                        note = nucleotide sequence of terminator IDP1t
                        organism = synthetic construct
SEQUENCE: 39
tcgaatttac gtagcccaat ctaccacttt tttttttcat tttttaaagt gttatactta  60
gttatgctct aggataatga actacttttt tttttttttt tttactgtta tcataaatat  120
atataccttta ttgttgtttg caaccgtcgg ttaattcctt atcaaggttc cccaagttcg  180
gatcattacc atcaatttcc aacattttca tgagttcttc ttcttcatta ccgtgtttta  240
gggggctgtt cgcacttcta atagggctat caccaagctg ttctaattcg tccaaaagtt  300
cagtaacacg atctttatgc tttagctcgt cataatcttt caattcataa atatttacaa  360
tttcgtctac gatattaaat tgcctcttgt aggtgcctat cttttcctta tgctcttcat  420
tttcaccgtt ttcttgaaac caaacaccga actcactacg ca                    462

SEQ ID NO: 40           moltype = DNA  length = 1000
FEATURE                 Location/Qualifiers
source                  1..1000
                        mol_type = other DNA
                        note = nucleotide sequence of promoter module pBM16A-GPM1p
                        organism = synthetic construct
SEQUENCE: 40
aatgctacta ttttggagat taatctcagt acaaaacaat attaaaaaga ggtgaattat  60
ttttcccccc ttattttttt tttgttaaaa ttgatccaaa tgtaaataaa caatcacaag  120
gaaaaaaaaa aaaaaaaaaa aaatagccgc catgaccccg gatcgtcggt tgtgatacgg  180
tcagggtagc gccctggtca aacttcagaa ctaaaaaaat aataaggaag aaaaaaaatag  240
ctaatttttc cggcagaaag attttcgcta cccgaaagtt tttccggcaa gctaaatgga  300
aaaaggaaag attattgaaa gagaaagaaa gaaaaaaaaa aaatgtacac ccagacatcg  360
ggcttccaca atttcggctc tattgttttc catctctcgc aacggcggga ttcctctatg  420
gcgtgtgatg tctgtatctg ttacttaatc cagaaactgg cacttgaccc aactctgcca  480
cgtgggtcgt tttgccatcg acagattggg agattttcat agtagaattc agcatgatag  540
ctacgtaaat gtgttccgca ccgtcacaaa gtgttttcta ctgttctttc ttctttcgtt  600
cattcagttg agttgagtga gtgctttgtt caatggatct tagctaaaat gcatattttt  660
tctcttggta aatgaatgct tgtgatgtct tccaagtgat ttcctttcct tcccatatga  720
tgctaggtac ctttagtgtc ttcctaaaaa aaaaaaaagg ctcgccatca aaacgatatt  780
cgttggcttt tttttctgaa ttataaatac tctttggtaa cttttcattt ccaagaacct  840
cttttttcca gttatatcat ggtccccttt caaagttatt ctctactctt tttcatattc  900
attctttttc atcctttggt tttttattct taacttgttt attattctct cttgtttcta  960
tttacaagac accaatcaaa acaaataaaa catcatcaca                      1000

SEQ ID NO: 41           moltype = DNA  length = 500
FEATURE                 Location/Qualifiers
source                  1..500
                        mol_type = other DNA
                        note = nucleotide sequence of ASP3t
                        organism = synthetic construct
SEQUENCE: 41
agcctgatca gtgacttttc atcacactgt gtttttatat agttcttagt agtaaatata  60
ctctataatt tctacatcct tttcatgatg tgccagttaa gctattttta gcaaacaaaa  120
agatgaattt gagtattgag cacatcattc actgttcagc tgatacaaaa catatgattt  180
ctaatattca cataggaaaa atcgctccaa acatcgaagt atcatcgcta ctttggtctt  240
ttatctgctt ctcttctctt cgctcttttc actgctcgtg ccgctgcaac gctccaactc  300
agttctatct cagctccttc cccttatccc ttgagcagtg tcaaggcgag gctgcgtgat  360
gtattcgtgc gcgaaaaaaa aaacaactgc agcacctgag tttcgcgtat ggtcacccac  420
tacactactc ggtcaggctc ttaccagctt aactacagtt gatcggacgg gaaacggtgc  480
tttctggtag atatggccgc                                             500

SEQ ID NO: 42           moltype = DNA  length = 492
FEATURE                 Location/Qualifiers
source                  1..492
                        mol_type = other DNA
                        note = nucleotide sequence MDM35t
                        organism = synthetic construct
SEQUENCE: 42
tttagcacag aatgtgcatt attcaacatg taaatactaa tactgcaata tcgacttata  60
ataatgtata gtgatccgta tattaataga tctgtttcaa ttctttacct ttttaggata  120
tccgtcaccc gtgattccgt cggaggtgag cactcgccca aataaataac gggaaatggt  180
ggcaaaaagt agtggcggga aaaggaaaaa ttttcgttct ctcccatata aacgtttcat  240
tccttttcct aagtctttta cagtaatttc agaaacattc gtattttata tttgatcttt  300
tgaagctaca agaaaaactc ttaccaatta ccccaaaaaa atcaccatca taaagtactt  360
acatatttat ttttgtttgg tcgttttctc aatataatct acatcatcat atatatataa  420
tgtctacaca atttaggaag tctaatcata atagtcatag tagtaaaaaa ctaaatcctg  480
cgctaaagtc ca                                                     492

SEQ ID NO: 43           moltype = DNA  length = 711
FEATURE                 Location/Qualifiers
source                  1..711
                        mol_type = other DNA
                        note = nucleotide sequence of delta 22site1 plasmid
                        organism = synthetic construct
```

```
SEQUENCE: 43
caccggagct tggatatgat aaacgaaata ttcttgaatc gtgagatcgc ctgttttcaa  60
aaccgttgga ggcagaaaca attttgtcac aagatgggca ttctacccca tccttgctgt  120
attattgtag tctcgctttc ttttatgctg gacaaatgag actactgcac atttttatac  180
gttcttggtt ttttttaaag gtgtggtttc ggcattatcc tgccgcacgt ttcttggata  240
attcatcctg attctctatt ttaaacgctt cagcctatca ggatttggtt ttgatacata  300
ctgcaagagt gtatctcggg aacagtcatt tattccgcaa caaacttaat tgcggaacgc  360
gttaggcgat ttctagcata tatcaaatac cgttcgcgat ttcttctggg ttcgtctctt  420
ttcttttaaa tacttattaa cgtactcaaa caactacact tcgttgtatc tcagaatgag  480
atccctcagt atgacaatac atcattctaa acgttcgtaa aacacatatg aaacaacttt  540
ataacaaagc gaacaaaatg ggcaacatga gatgaaactc cgcgtccctt agctgaacta  600
cccaaacgta cgaatgcctg aacaattagt ttagatccga gattccgcgc ttccatcatt  660
tagtataatc catattttat ataatatata ggataagtaa cagcccgcga a           711

SEQ ID NO: 44          moltype = DNA  length = 653
FEATURE                Location/Qualifiers
source                 1..653
                       mol_type = other DNA
                       note = nucleotide sequence of delta 22site2 plasmid
                       organism = synthetic construct
SEQUENCE: 44
ggaccaacta tcatccgcta attactgaca ttaccaaatg agatctgtga atgggcaaga  60
taaaaaacaa aaattgaaat gtttgacgtt atgtaaaact attaattcct tcgctttcgg  120
cggtcacaga atttgcgtgt agctgactct tgttcaatca atatcatttg ttactttatt  180
tgaaagtctg tattactgcg cctattgtca tccgtaccaa agaacgtcaa aaagaaacaa  240
gataattttt gtgcttacac catttataga tcactgagcc cagaatatcg ctggagctca  300
gtgtaagtgg catgaacaca actctgactg atcgcacata ttgccgttat cataaatact  360
agttgtactt gtcaatgcga cgaatggcat catgcctatt attacgttcc tctttttccg  420
tttcatgttt ccagaatgct attgaatcta acacttcaat tataaaaaag aataaatccg  480
caataatttt aggctaattg ttgtactgtc aagcgaacct aatggttaaa attcagagga  540
accttcgacg tagtctgatc gctacttcta tatcttatgt tcccagtcaa tcaaaagttg  600
atactataat agctgccatt tatacctgtt agttatggcg atcgtttatc acg         653

SEQ ID NO: 45          moltype = DNA  length = 1467
FEATURE                Location/Qualifiers
source                 1..1467
                       mol_type = other DNA
                       note = nucleotide sequence of functional gene Kas
                       organism = synthetic construct
SEQUENCE: 45
atgtcttcta tcacttcttc ttgttactct aacttgatct tgaagaagaa ggaatctaga  60
atcaacggtg gtttccactt gcaatacaac ggtttgagag ctatcgaatc tgttcaaatg  120
ccagcttctt ctgttgctta caagccaaag gttgttaagt ggggtagaat cagagttatg  180
gcttctccag ctgtttctgc tccaaagaga gaaactgacc caaagaagag aatcgttatc  240
actggtatgg gtttggtttc tgttttcggt tctgacatcg acaacttcta caacaagttg  300
ttggaaggtc aatctggtat ctctttgatc gacagattcg acgcttcttc ttacactgtt  360
agattcgctg gtcaaatcag agacttctct tctgaaggtt acatcgacgg taagaacgac  420
agaagattgg acgactgttg gagatactgt ttggttgctg gtaagagagc tttggaagac  480
gctaacctcg gtcagcaagt actagacact atggacaaga ctagaatcgg tgtttttggtt  540
ggttcttcta tgggtggttc taaggttttc gctgacgctg ttgaagcttt ggttcaaaga  600
ggttacaaga agatcaaccc attcttcatc ccatactcta tcactaacat gggttctgct  660
ttgttggcta tcgacactgg tttgatgggt ccaacttact ctatctctac tgcttgtgct  720
actgctaact actgtttcta cgcttctgct aaccacatca gaagaggtga agctgacatc  780
atggttgctg gtggtactga cgctttcatc tctgctatcg gtgttggtgg tttgatcgct  840
tgccgtgcgt tgtctcaaag aaatgacgaa tacgaaaagg cttctagacc atgggacaga  900
aacagagacg gtttcgttat cggtgaaggt tctggtgttt tggttatgga aaacttggaa  960
cacgctttga agagaggtgc tccaatcatc gctgaatact tgggtggtgc tatcacttgt  1020
gacgctcacc acatcactga cccaagagct gacggtttgg gtgtttcttc ttgtatcgtt  1080
atgtctttgg ttgacgctgg tgtttctcca gaagaagtta actacatcaa cgctcacgct  1140
acttctactt tggctggtga cttggctgaa gttaacgcta tcaagaaggt tttcaaggac  1200
acttctgaaa tcaagatgaa cggtactaag tctatgatcg gtcacggttt gggtgcttct  1260
ggtggtttgg aagctatcgc tactatcaag gctatcacta ctggttggtt gcacccaact  1320
atcaaccaat acgacttgga accacaagtt actatcgaca ctgttccaaa cgttaagaag  1380
caacacgaag ttaacgttgg tatctctaac tctttcggtt tcggtggtca caattctgtt  1440
gttgtcttcg ccccatacaa gccataa                                     1467

SEQ ID NO: 46          moltype = DNA  length = 399
FEATURE                Location/Qualifiers
source                 1..399
                       mol_type = other DNA
                       note = nucleotide sequence of functional gene Acl
                       organism = synthetic construct
SEQUENCE: 46
atggcttcta tcactgcttc ttctttcgct atctcttctt tcaagcacaa ccaaatctgt  60
ttgaagtcgt cgagcttgcc aatcaagggc atctctttcc catctttgag aatgaagcca  120
gctactagaa gattgtctat caactgtgct gctaagccag aaactgttga caaggtttgt  180
gctatcgtta agaagcaatt ggctttgcca ggtgactctg ttgttaacgg tgaatctaag  240
tttgctgctc tcggtgctga ctcgttggac actgttgaaa tcgttatggg tttggaagaa  300
gctttcggta tcactgttga agaagaaaac gctcaaacta tcgctactgt tcaagacgct  360
```

```
gctgacttga tcgaagactt ggttgctaag aagtgttaa                       399

SEQ ID NO: 47          moltype = DNA  length = 1116
FEATURE                Location/Qualifiers
source                 1..1116
                       mol_type = other DNA
                       note = nucleotide sequence of functional gene Fat
                       organism = synthetic construct
SEQUENCE: 47
atgttgtcta gaggttcttt cttgaagaac gttgctatcg gtgaccacaa ccaatgtact  60
aagagattct tcaactctaa ctctgtttct atcggttgta gaaagccagt tatctcttct  120
tcttcttctt ctgttggtgt tagatctggt ccagttttgg ctgttgctac taacgaaaga  180
gaatctaagt ctaagcaaca agtttctcac gaaccatctt tggctgacag attgagattg  240
ggtactatgt ctgaagacgg tatgtcttac aaggaaaagt tcatcgttag atgttacgaa  300
gttggtgtta acaagacttt gactgttgaa actatcgcta acttgttgca agaagttggt  360
tgtaaccacg ctcaatctgt tggtttctct actgacggtt tcgctactac tcactctatg  420
agaaagttgc acttgatctg ggttactgct agaatgtaca tcgaaatcta caagtaccca  480
gcttggtctg acgttgttga aatcgaaact tggtgtcaat ctgaaggtag aatcggtact  540
agaagagact ggatcttgaa ggactgtgct actggtgaag ttatcggtag agctacttct  600
aagtggttga tgatgaacca agacactaga agattgcaaa aggttactga cgaagttaga  660
gacgaattgg aattgtactt cccaaaggaa ttgagattgg ctttcccaga agaaaacaac  720
ggttctttga agaagatccc aaagttggaa gacccagctg aatactctaa gctcggcttg  780
gttccaagac gtgctgactt ggacatgaac caacacgtta acaacgttac ttacatcggt  840
tgggttttgg aatctatgcc acaagaaatc atcgacactc acgaattggg tactatcact  900
atcgactaca gaagagaatg tcaacacgac gacgttgttg acagcttgac ttctgttgag  960
ccaatcgaag acactgacgc tttgggtgct aacggttctg ctactgctgc taaggacgtt  1020
aacaagtctg ttttgcactt cttgagattg tcttctgacg gtttggaaat caacagatgt  1080
agaactgaat ggagaaagaa gccatctaga atctaa                          1116

SEQ ID NO: 48          moltype = DNA  length = 1323
FEATURE                Location/Qualifiers
source                 1..1323
                       mol_type = other DNA
                       note = nucleotide sequence of functional gene AT3
                       organism = synthetic construct
SEQUENCE: 48
atggctttcg ctttgccatc ttctttggtt tctgtttgtg acaagtcttt catcaagcca  60
tcttctttga ctccatctac tttgagattc cacaagttgt ctttcatcga ccaatctttg  120
tctaacatgt acatcccatg cgcgttcttc tacccaaagg ttcaacaaag attggaagac  180
tctaagaact ctgacgaatt gtctcacatc gctcacttgt tgcaaacttc tttgtctcaa  240
actttggttt cttactaccc atacgctggt aagttgaagg acaacgctac tgttgactgt  300
aacgacatgg gtgctgaatt cttgtctgtt agaatcaagt gttctatgtc tgaaatcttg  360
gaccacccac acgcttcttt ggctgaatct atcgttttgc caaaggactt gccatgggct  420
aacaactgtg aaggtggtaa cttgttggtt gttcaagttt ctaagttcga ctgtggtggt  480
atcgctatct ctgtttgttt ctctcacaag atcggtgacg gttgttcttt gttgaacttc  540
ttgaacgact ggtcttctgt tactagagac ccaactacta ctactttggt tccatctcca  600
agattcgttg gtgactctgt tttctctact caaaagtacg gttctttgat cactccacaa  660
atcttgtctg acttgaacca atgtgttcaa aagagattga tcttcccaac tgacaagctc  720
gacgctctca gagctaaggt tgctgaagaa tctggtgtta agaacccaac tagagctgaa  780
gttgttagtg cgcttttgtt taaatgtgct actaaggctt cttcttctat gttgccatct  840
aagttggttc acttcttgaa catcagaact atgatcaagc caagattgcc aagaaacgct  900
atcggtaact tgtcttctat cttctctatc gaagctacta acatgcaaga catggaattg  960
ccaactttgg ttagaaactt gagaaaggaa gttgaagttg cttacaagaa ggaccaagtt  1020
gaacaaaacg aattgatctt ggaagttgtt gaatctatga gagaaggtaa gttgccattc  1080
gaaaacatgg acggttacaa gaacgtttac acttgttcta acttgtgtaa gtacccatac  1140
tacactgttg acttcggttg gggtagacca gaaagagttt gtttgggtaa cggtccatct  1200
aagaacgctt tcttcttgaa ggactacaag gctggtcaag gtgttgaagc tagagttatg  1260
ttgcacaagc aacaaatgtc tgaattcgaa agaaacgaag aattggttga attcatcgct  1320
taa                                                              1323

SEQ ID NO: 49          moltype = DNA  length = 437
FEATURE                Location/Qualifiers
source                 1..437
                       mol_type = other DNA
                       note = nucleotide sequence of HAP4t
                       organism = synthetic construct
SEQUENCE: 49
aataggcatg ttgcaataaa acgaaaacaa ctaaaaatca cgaaaacaaa atgatattat  60
acaataaaaa attcttatta tgggtaatga tagtattctt cgcctgctta ggcgtccttt  120
tccttcaaca acaaaaattc caaaaaaaaa aagtaaaaaa acaaaacttt gattgttttt  180
taatgatgtt aatgattttt tttttctttc tttatcataa aaaaaaagtt aaaatgaaaa  240
acaaatatgg gtctggaagg ccattatttt ttttttattt atataccgtt tctggtactt  300
agttatttat tctcatacat acactatatt caaattacct aagagcattt tcacatatcc  360
gtttactttc attttttttt tttttgcttc ctttttacat atcttccgta tatcacatca  420
cgtttacgcg tatggtg                                               437

SEQ ID NO: 50          moltype = DNA  length = 434
FEATURE                Location/Qualifiers
source                 1..434
```

```
                        mol_type = other DNA
                        note = nucleoside sequence of YCP4t
                        organism = synthetic construct
SEQUENCE: 50
gaaacaacag ttcgcgtcta atatttagtt cttactaaca ttaattctat ctcagcagat  60
atatcaatgt aggacgttgg aaaattaata aagaattaac tctttttatt ttattttttc  120
ctttttatat taaaagtata tttctgtaag tccttgtact aataatatca tttcctaata  180
ttttgaaata tagttgtttt ttgtcaagca aaactcttga tttcaaagac ctcattttgt  240
taagccaaaa gcgaaaaatt ctatttcgac ttttctttct gtttccgctc cttgtattct  300
accattgatg ctgtcttaaa caataaatat acagtttgaa attaagtttc tatatacagg  360
cttaagttta tttaaaaagg aaaccactag atgaaagatg agcctagtcc ttttttaaag  420
tccgaacgcg acgt                                                  434

SEQ ID NO: 51           moltype = DNA  length = 35
FEATURE                 Location/Qualifiers
source                  1..35
                        mol_type = other DNA
                        note = Primer 1
                        organism = synthetic construct
SEQUENCE: 51
cctgctcttc acattttgtt tatgtgtgtt tattc                          35

SEQ ID NO: 52           moltype = DNA  length = 59
FEATURE                 Location/Qualifiers
source                  1..59
                        mol_type = other DNA
                        note = Primer 2
                        organism = synthetic construct
SEQUENCE: 52
tctgttctat tgtatatctc ccctccgcca cctacatgta tactagcgtt gaatgttag   59

SEQ ID NO: 53           moltype = DNA  length = 59
FEATURE                 Location/Qualifiers
source                  1..59
                        mol_type = other DNA
                        note = Primer 3
                        organism = synthetic construct
SEQUENCE: 53
aaacttcttg ttgttgacgc taacattcaa cgctagtata catgtaggtg gcggagggg   59

SEQ ID NO: 54           moltype = DNA  length = 36
FEATURE                 Location/Qualifiers
source                  1..36
                        mol_type = other DNA
                        note = Primer 4
                        organism = synthetic construct
SEQUENCE: 54
cctgctcttc atgtatatga gatagttgat tgtatg                         36

SEQ ID NO: 55           moltype = DNA  length = 37
FEATURE                 Location/Qualifiers
source                  1..37
                        mol_type = other DNA
                        note = Primer 5
                        organism = synthetic construct
SEQUENCE: 55
cctgctcttc acattgtttt atatttgttg taaaaag                        37

SEQ ID NO: 56           moltype = DNA  length = 59
FEATURE                 Location/Qualifiers
source                  1..59
                        mol_type = other DNA
                        note = Primer 6
                        organism = synthetic construct
SEQUENCE: 56
ggaagcgcct acgcttgaca tctactatat gtaagtataa cgcacagata ttataacat   59

SEQ ID NO: 57           moltype = DNA  length = 59
FEATURE                 Location/Qualifiers
source                  1..59
                        mol_type = other DNA
                        note = Primer 7
                        organism = synthetic construct
SEQUENCE: 57
gcaaatgcct attgtgcaga tgttataata tctgtgcgtt atacttacat atagtagat   59

SEQ ID NO: 58           moltype = DNA  length = 39
FEATURE                 Location/Qualifiers
source                  1..39
```

```
                      mol_type = other DNA
                      note = Primer 8
                      organism = synthetic construct
SEQUENCE: 58
cctgctcttc atgtggtact agtgtttagt taattatag                          39

SEQ ID NO: 59         moltype = DNA  length = 42
FEATURE               Location/Qualifiers
source                1..42
                      mol_type = other DNA
                      note = Primer 9
                      organism = synthetic construct
SEQUENCE: 59
cctgctcttc aggtttaaca aattggaata ggagcaccgt tc                      42

SEQ ID NO: 60         moltype = DNA  length = 38
FEATURE               Location/Qualifiers
source                1..38
                      mol_type = other DNA
                      note = Primer 10
                      organism = synthetic construct
SEQUENCE: 60
cctgctcttc agtaatggac caaattgagg caatgttg                           38

SEQ ID NO: 61         moltype = DNA  length = 38
FEATURE               Location/Qualifiers
source                1..38
                      mol_type = other DNA
                      note = Primer 11
                      organism = synthetic construct
SEQUENCE: 61
cctgctcttc aacaatggac ttgttgttgt tggaaaag                           38

SEQ ID NO: 62         moltype = DNA  length = 38
FEATURE               Location/Qualifiers
source                1..38
                      mol_type = other DNA
                      note = Primer 12
                      organism = synthetic construct
SEQUENCE: 62
cctgctcttc agatttaaca atttcttggc ttcataac                           38

SEQ ID NO: 63         moltype = DNA  length = 38
FEATURE               Location/Qualifiers
source                1..38
                      mol_type = other DNA
                      note = Primer 13
                      organism = synthetic construct
SEQUENCE: 63
cctgctcttc aggtttaaca taacttagct tttaaatc                           38

SEQ ID NO: 64         moltype = DNA  length = 36
FEATURE               Location/Qualifiers
source                1..36
                      mol_type = other DNA
                      note = Primer 14
                      organism = synthetic construct
SEQUENCE: 64
cctgctcttc agtaatgatt actgcagcat tgcacg                             36

SEQ ID NO: 65         moltype = DNA  length = 37
FEATURE               Location/Qualifiers
source                1..37
                      mol_type = other DNA
                      note = Primer 15
                      organism = synthetic construct
SEQUENCE: 65
cctgctcttc aacaatgaaa attgaagtta aagaatc                            37

SEQ ID NO: 66         moltype = DNA  length = 42
FEATURE               Location/Qualifiers
source                1..42
                      mol_type = other DNA
                      note = Primer 16
                      organism = synthetic construct
SEQUENCE: 66
cctgctcttc agatttaaaa atcgtacaaa aatttctcaa ac                      42

SEQ ID NO: 67         moltype = DNA  length = 37
```

```
FEATURE                Location/Qualifiers
source                 1..37
                       mol_type = other DNA
                       note = Primer 17
                       organism = synthetic construct
SEQUENCE: 67
cctgctcttc acatggtctc acatctatta ttgtatg                           37

SEQ ID NO: 68          moltype = DNA  length = 59
FEATURE                Location/Qualifiers
source                 1..59
                       mol_type = other DNA
                       note = Primer 18
                       organism = synthetic construct
SEQUENCE: 68
ttgtacatac taatatatat aaacaaagta acgtctccta cgcggcgtta tgtcactaa   59

SEQ ID NO: 69          moltype = DNA  length = 59
FEATURE                Location/Qualifiers
source                 1..59
                       mol_type = other DNA
                       note = Primer 19
                       organism = synthetic construct
SEQUENCE: 69
cgcaagttgg tgcacgtcgt tagtgacata acgccgcgta ggagacgtta ctttgttta   59

SEQ ID NO: 70          moltype = DNA  length = 36
FEATURE                Location/Qualifiers
source                 1..36
                       mol_type = other DNA
                       note = Primer 20
                       organism = synthetic construct
SEQUENCE: 70
cctgctcttc atgtataatt tgcgatcgta gttggg                            36

SEQ ID NO: 71          moltype = DNA  length = 37
FEATURE                Location/Qualifiers
source                 1..37
                       mol_type = other DNA
                       note = Primer 21
                       organism = synthetic construct
SEQUENCE: 71
cctgctcttc aggtttaaga tattcttctg cacaaag                           37

SEQ ID NO: 72          moltype = DNA  length = 39
FEATURE                Location/Qualifiers
source                 1..39
                       mol_type = other DNA
                       note = Primer 22
                       organism = synthetic construct
SEQUENCE: 72
cctgctcttc agtaatggct actaacggta gacaccaag                         39

SEQ ID NO: 73          moltype = DNA  length = 36
FEATURE                Location/Qualifiers
source                 1..36
                       mol_type = other DNA
                       note = Primer 23
                       organism = synthetic construct
SEQUENCE: 73
cctgctcttc aacaatgtct gatgaattga catttg                            36

SEQ ID NO: 74          moltype = DNA  length = 37
FEATURE                Location/Qualifiers
source                 1..37
                       mol_type = other DNA
                       note = Primer 24
                       organism = synthetic construct
SEQUENCE: 74
cctgctcttc agatttaatc ttctcttcta taaccac                           37

SEQ ID NO: 75          moltype = DNA  length = 59
FEATURE                Location/Qualifiers
source                 1..59
                       mol_type = other DNA
                       note = Primer 25
                       organism = synthetic construct
SEQUENCE: 75
cttgtattgt tctaacgatc cgaccatttc atcctgaata taacaatact gacagtact   59
```

```
SEQ ID NO: 76          moltype = DNA  length = 59
FEATURE                Location/Qualifiers
source                 1..59
                       mol_type = other DNA
                       note = Primer 26
                       organism = synthetic construct
SEQUENCE: 76
catatcatga cccataaatt cgtttgtaat atttgccatt ttgaatatgt attacttgg   59

SEQ ID NO: 77          moltype = DNA  length = 59
FEATURE                Location/Qualifiers
source                 1..59
                       mol_type = other DNA
                       note = Primer 27
                       organism = synthetic construct
SEQUENCE: 77
ttgtcatata taaccataac caagtaatac atattcaaaa tggcaaatat tacaaacga   59

SEQ ID NO: 78          moltype = DNA  length = 59
FEATURE                Location/Qualifiers
source                 1..59
                       mol_type = other DNA
                       note = Primer 28
                       organism = synthetic construct
SEQUENCE: 78
cgagtaaaaa aagagctgca gttcccagga agcgttaaat tattgttttt gtgacttca   59

SEQ ID NO: 79          moltype = DNA  length = 59
FEATURE                Location/Qualifiers
source                 1..59
                       mol_type = other DNA
                       note = Primer 29
                       organism = synthetic construct
SEQUENCE: 79
gaaaaaagag ttgaagaatt gaagtcacaa aaacaataat ttaacgcttc ctgggaact   59

SEQ ID NO: 80          moltype = DNA  length = 59
FEATURE                Location/Qualifiers
source                 1..59
                       mol_type = other DNA
                       note = Primer 30
                       organism = synthetic construct
SEQUENCE: 80
gtgatgaatt ttgagagccc acttttgttg gggacgattg agaggctgaa ggcagagaa   59

SEQ ID NO: 81          moltype = DNA  length = 59
FEATURE                Location/Qualifiers
source                 1..59
                       mol_type = other DNA
                       note = Primer 31
                       organism = synthetic construct
SEQUENCE: 81
gcatccacat cttcacatga aaatagaggc caatcaggca ggagacgtta ctttgttta   59

SEQ ID NO: 82          moltype = DNA  length = 59
FEATURE                Location/Qualifiers
source                 1..59
                       mol_type = other DNA
                       note = Primer 32
                       organism = synthetic construct
SEQUENCE: 82
tttctctcgc agcgccagta acgggttttc cgatgtcata taatttgcga tcgtagttg   59

SEQ ID NO: 83          moltype = DNA  length = 59
FEATURE                Location/Qualifiers
source                 1..59
                       mol_type = other DNA
                       note = Primer 33
                       organism = synthetic construct
SEQUENCE: 83
tacatacaca acataaaccc aactacgatc gcaaattata tgacatcgga aaacccgtt   59

SEQ ID NO: 84          moltype = DNA  length = 59
FEATURE                Location/Qualifiers
source                 1..59
                       mol_type = other DNA
                       note = Primer 34
                       organism = synthetic construct
```

```
SEQUENCE: 84
ctgataataa aaacggtatg cctacacata cacgctttat caggttggat caacaggca   59

SEQ ID NO: 85          moltype = DNA  length = 59
FEATURE                Location/Qualifiers
source                 1..59
                       mol_type = other DNA
                       note = Primer 35
                       organism = synthetic construct
SEQUENCE: 85
tacccaagtg agaacgtagt gcctgttgat ccaacctgat aaagcgtgta tgtgtaggc   59

SEQ ID NO: 86          moltype = DNA  length = 59
FEATURE                Location/Qualifiers
source                 1..59
                       mol_type = other DNA
                       note = Primer 36
                       organism = synthetic construct
SEQUENCE: 86
attatattat atgggtctgc aaggtagagg cgcgcttgtg cagcgatcag caataatga   59

SEQ ID NO: 87          moltype = DNA  length = 59
FEATURE                Location/Qualifiers
source                 1..59
                       mol_type = other DNA
                       note = Primer 37
                       organism = synthetic construct
SEQUENCE: 87
attccgcgtt tgcttcattt cattattgct gatcgctgca caagcgcgcc tctaccttg   59

SEQ ID NO: 88          moltype = DNA  length = 59
FEATURE                Location/Qualifiers
source                 1..59
                       mol_type = other DNA
                       note = Primer 38
                       organism = synthetic construct
SEQUENCE: 88
ggaagtgtaa tcaacagggg gggcagaacc agcagtcatt gttaattcag taaattttc   59

SEQ ID NO: 89          moltype = DNA  length = 59
FEATURE                Location/Qualifiers
source                 1..59
                       mol_type = other DNA
                       note = Primer 39
                       organism = synthetic construct
SEQUENCE: 89
ctttttttctt cccaagatcg aaaatttact gaattaacaa tgactgctgg ttctgcccc   59

SEQ ID NO: 90          moltype = DNA  length = 59
FEATURE                Location/Qualifiers
source                 1..59
                       mol_type = other DNA
                       note = Primer 40
                       organism = synthetic construct
SEQUENCE: 90
cctctcctag cgtacacgga tggcaagaat aaactggctt caacttttat agttgtcaa   59

SEQ ID NO: 91          moltype = DNA  length = 59
FEATURE                Location/Qualifiers
source                 1..59
                       mol_type = other DNA
                       note = Primer 41
                       organism = synthetic construct
SEQUENCE: 91
agtggcataa aagaattttt tgacaactat aaaagttgaa gccagtttat tcttgccat   59

SEQ ID NO: 92          moltype = DNA  length = 58
FEATURE                Location/Qualifiers
source                 1..58
                       mol_type = other DNA
                       note = Primer 42
                       organism = synthetic construct
SEQUENCE: 92
agctgaaatg caaggattga taaaataata ggataataga agaatggatc aaaatggc    58

SEQ ID NO: 93          moltype = DNA  length = 59
FEATURE                Location/Qualifiers
source                 1..59
                       mol_type = other DNA
```

```
                        note = Primer 43
                        organism = synthetic construct
SEQUENCE: 93
ataacatctt ttttttattc cttctttgat attttgtcaa actgtgggaa tactcaggt   59

SEQ ID NO: 94           moltype = DNA  length = 59
FEATURE                 Location/Qualifiers
source                  1..59
                        mol_type = other DNA
                        note = Primer 44
                        organism = synthetic construct
SEQUENCE: 94
aacacgcagg ggcccgaaat tgttcctacg agaagtagtt gcttacctgt attcctttta   59

SEQ ID NO: 95           moltype = DNA  length = 59
FEATURE                 Location/Qualifiers
source                  1..59
                        mol_type = other DNA
                        note = Primer 45
                        organism = synthetic construct
SEQUENCE: 95
aggagaaaaa ggaggatagt aaaggaatac aggtaagcaa ctacttctcg taggaacaa   59

SEQ ID NO: 96           moltype = DNA  length = 59
FEATURE                 Location/Qualifiers
source                  1..59
                        mol_type = other DNA
                        note = Primer 46
                        organism = synthetic construct
SEQUENCE: 96
agacaatctg tcagcttgtc tttcaacaac ttgagtcatt ttttaatttt aatcaaaaa   59

SEQ ID NO: 97           moltype = DNA  length = 59
FEATURE                 Location/Qualifiers
source                  1..59
                        mol_type = other DNA
                        note = Primer 47
                        organism = synthetic construct
SEQUENCE: 97
aacacaaaaa caaaaagttt ttttaatttt aatcaaaaaa tgactcaagt tgttgaaag   59

SEQ ID NO: 98           moltype = DNA  length = 59
FEATURE                 Location/Qualifiers
source                  1..59
                        mol_type = other DNA
                        note = Primer 48
                        organism = synthetic construct
SEQUENCE: 98
ttttgtatag ctgcaacctt caatctgcaa ataagcttct taaccgaagt ccttaccgt   59

SEQ ID NO: 99           moltype = DNA  length = 60
FEATURE                 Location/Qualifiers
source                  1..60
                        mol_type = other DNA
                        note = Primer 49
                        organism = synthetic construct
SEQUENCE: 99
tttgttggtt gacgaagctg acggtaagga cttcggttaa gaagcttatt tgcagattga  60

SEQ ID NO: 100          moltype = DNA  length = 59
FEATURE                 Location/Qualifiers
source                  1..59
                        mol_type = other DNA
                        note = Primer 50
                        organism = synthetic construct
SEQUENCE: 100
ttgtacatac taatatatat aaacaaagta acgtctcctg cctgattggc ctctatttt   59

SEQ ID NO: 101          moltype = DNA  length = 59
FEATURE                 Location/Qualifiers
source                  1..59
                        mol_type = other DNA
                        note = Primer 51
                        organism = synthetic construct
SEQUENCE: 101
tatagacaca caaacacaaa tacacacact aaattaataa tgtctgctcc agctcaaaa   59

SEQ ID NO: 102          moltype = DNA  length = 59
FEATURE                 Location/Qualifiers
```

```
source                  1..59
                        mol_type = other DNA
                        note = Primer 52
                        organism = synthetic construct
SEQUENCE: 102
taagaacagg aagggatgac gtaggaacct tgtgctagat caatatctgt agtggtcgg   59

SEQ ID NO: 103          moltype = DNA  length = 59
FEATURE                 Location/Qualifiers
source                  1..59
                        mol_type = other DNA
                        note = Primer 53
                        organism = synthetic construct
SEQUENCE: 103
cataacacca agcaactaat actataacat acaataataa tggaaacttt cttgttcac   59

SEQ ID NO: 104          moltype = DNA  length = 59
FEATURE                 Location/Qualifiers
source                  1..59
                        mol_type = other DNA
                        note = Primer 54
                        organism = synthetic construct
SEQUENCE: 104
atcaagattt tttttgtttt tttttacaat tgagtagact taagcttgtg gcttgtccc   59

SEQ ID NO: 105          moltype = DNA  length = 59
FEATURE                 Location/Qualifiers
source                  1..59
                        mol_type = other DNA
                        note = Primer 55
                        organism = synthetic construct
SEQUENCE: 105
accctgccct catatcacct gcgtttccgt taaactatcc tagtacactc tatattttt   59

SEQ ID NO: 106          moltype = DNA  length = 59
FEATURE                 Location/Qualifiers
source                  1..59
                        mol_type = other DNA
                        note = Primer 56
                        organism = synthetic construct
SEQUENCE: 106
gccaagtagg caattattta gtactgtcag tattgttatc ctgatgcggt attttctcc   59

SEQ ID NO: 107          moltype = DNA  length = 59
FEATURE                 Location/Qualifiers
source                  1..59
                        mol_type = other DNA
                        note = Primer 57
                        organism = synthetic construct
SEQUENCE: 107
ataccgcaca gatgcgtaag gagaaaatac cgcatcagga atttttttgg aaaaccaag   59

SEQ ID NO: 108          moltype = DNA  length = 59
FEATURE                 Location/Qualifiers
source                  1..59
                        mol_type = other DNA
                        note = Primer 58
                        organism = synthetic construct
SEQUENCE: 108
gatatcagcg attttgtagt tttgagctgg agcagacatt attaatttag tgtgtgtat   59

SEQ ID NO: 109          moltype = DNA  length = 59
FEATURE                 Location/Qualifiers
source                  1..59
                        mol_type = other DNA
                        note = Primer 59
                        organism = synthetic construct
SEQUENCE: 109
ctcctttatt tgttctttgt cttttgactt cttcccgcta cgcggcgtta tgtcactaa   59

SEQ ID NO: 110          moltype = DNA  length = 59
FEATURE                 Location/Qualifiers
source                  1..59
                        mol_type = other DNA
                        note = Primer 60
                        organism = synthetic construct
SEQUENCE: 110
ttcgttaaca gattcagaag tgaacaagaa agtttccatt attattgtat gttatagta   59
```

```
SEQ ID NO: 111         moltype = DNA  length = 59
FEATURE                Location/Qualifiers
source                 1..59
                       mol_type = other DNA
                       note = Primer 61
                       organism = synthetic construct
SEQUENCE: 111
gaagaaggtc cattcaaggc cgaccactac agatattgat ctagcacaag gttcctacg   59

SEQ ID NO: 112         moltype = DNA  length = 59
FEATURE                Location/Qualifiers
source                 1..59
                       mol_type = other DNA
                       note = Primer 62
                       organism = synthetic construct
SEQUENCE: 112
cgcaagttgg tgcacgtcgt tagtgacata acgccgcgta gcgggaagaa gtcaaaaga   59

SEQ ID NO: 113         moltype = DNA  length = 59
FEATURE                Location/Qualifiers
source                 1..59
                       mol_type = other DNA
                       note = Primer 63
                       organism = synthetic construct
SEQUENCE: 113
gttgttaagc cattgaagtg ggacaagcca caagcttaag tctactcaat tgtaaaaaa   59

SEQ ID NO: 114         moltype = DNA  length = 59
FEATURE                Location/Qualifiers
source                 1..59
                       mol_type = other DNA
                       note = Primer 64
                       organism = synthetic construct
SEQUENCE: 114
agactgtcaa ggagggtatt ctgggcctcc atgtcgctgc caagaggatc gagaaacca   59

SEQ ID NO: 115         moltype = DNA  length = 59
FEATURE                Location/Qualifiers
source                 1..59
                       mol_type = other DNA
                       note = Primer 65
                       organism = synthetic construct
SEQUENCE: 115
ttgtcatata taaccataac caagtaatac atattcaaaa tgaaaatcgg catcattgg   59

SEQ ID NO: 116         moltype = DNA  length = 59
FEATURE                Location/Qualifiers
source                 1..59
                       mol_type = other DNA
                       note = Primer 66
                       organism = synthetic construct
SEQUENCE: 116
aaaaaaaaaa aaaaattttt cagccatctg ttaagaaatt tagccatgtg caagtttct   59

SEQ ID NO: 117         moltype = DNA  length = 59
FEATURE                Location/Qualifiers
source                 1..59
                       mol_type = other DNA
                       note = Primer 67
                       organism = synthetic construct
SEQUENCE: 117
caagctatac caagcataca atcaactatc tcatatacaa tgccgttgtt agatagctt   59

SEQ ID NO: 118         moltype = DNA  length = 59
FEATURE                Location/Qualifiers
source                 1..59
                       mol_type = other DNA
                       note = Primer 68
                       organism = synthetic construct
SEQUENCE: 118
tgaaaaaaaa aagtggtaga ttgggctacg taaattcgac tagatgtgca gttcctgca   59

SEQ ID NO: 119         moltype = DNA  length = 59
FEATURE                Location/Qualifiers
source                 1..59
                       mol_type = other DNA
                       note = Primer 69
                       organism = synthetic construct
SEQUENCE: 119
```

```
ataccgcaca gatgcgtaag gagaaaatac cgcatcagga taacaatact gacagtact   59

SEQ ID NO: 120         moltype = DNA  length = 59
FEATURE                Location/Qualifiers
source                 1..59
                       mol_type = other DNA
                       note = Primer 70
                       organism = synthetic construct
SEQUENCE: 120
aacttcttct tccattgcac caatgatgcc gattttcatt ttgaatatgt attacttgg   59

SEQ ID NO: 121         moltype = DNA  length = 59
FEATURE                Location/Qualifiers
source                 1..59
                       mol_type = other DNA
                       note = Primer 71
                       organism = synthetic construct
SEQUENCE: 121
caggtgcagg ctgacctaat ggaattttta tggtcccgaa catgtaggtg gcggagggg   59

SEQ ID NO: 122         moltype = DNA  length = 59
FEATURE                Location/Qualifiers
source                 1..59
                       mol_type = other DNA
                       note = Primer 72
                       organism = synthetic construct
SEQUENCE: 122
ccgggtatga tcgactgtga agctatctaa caacggcatt gtatatgaga tagttgatt   59

SEQ ID NO: 123         moltype = DNA  length = 59
FEATURE                Location/Qualifiers
source                 1..59
                       mol_type = other DNA
                       note = Primer 73
                       organism = synthetic construct
SEQUENCE: 123
caccgttttc ttgaaaccaa acaccgaact cactacgcaa cgcggcgtta tgtcactaa   59

SEQ ID NO: 124         moltype = DNA  length = 59
FEATURE                Location/Qualifiers
source                 1..59
                       mol_type = other DNA
                       note = Primer 74
                       organism = synthetic construct
SEQUENCE: 124
gccaagtagg caattattta gtactgtcag tattgttatc ctgatgcggt attttctcc   59

SEQ ID NO: 125         moltype = DNA  length = 59
FEATURE                Location/Qualifiers
source                 1..59
                       mol_type = other DNA
                       note = Primer 75
                       organism = synthetic construct
SEQUENCE: 125
atggttgagt cactggtgca gaaacttgca catggctaaa tttcttaaca gatggctga   59

SEQ ID NO: 126         moltype = DNA  length = 59
FEATURE                Location/Qualifiers
source                 1..59
                       mol_type = other DNA
                       note = Primer 76
                       organism = synthetic construct
SEQUENCE: 126
tctgttctat tgtatatctc ccctccgcca cctacatgtt cgggaccata aaaattcca   59

SEQ ID NO: 127         moltype = DNA  length = 59
FEATURE                Location/Qualifiers
source                 1..59
                       mol_type = other DNA
                       note = Primer 77
                       organism = synthetic construct
SEQUENCE: 127
gcactgccga aagagaagtt gcaggaactg cacatctagt cgaatttacg tagcccaat   59

SEQ ID NO: 128         moltype = DNA  length = 59
FEATURE                Location/Qualifiers
source                 1..59
                       mol_type = other DNA
                       note = Primer 78
```

```
                        organism = synthetic construct
SEQUENCE: 128
cgcaagttgg tgcacgtcgt tagtgacata acgccgcgtt gcgtagtgag ttcggtgtt   59

SEQ ID NO: 129          moltype = DNA  length = 40
FEATURE                 Location/Qualifiers
source                  1..40
                        mol_type = other DNA
                        note = Primer 79
                        organism = synthetic construct
SEQUENCE: 129
cctgctcttc acattgtttt atatttgttg taaaaagtag                        40

SEQ ID NO: 130          moltype = DNA  length = 59
FEATURE                 Location/Qualifiers
source                  1..59
                        mol_type = other DNA
                        note = Primer 80
                        organism = synthetic construct
SEQUENCE: 130
gccaagtagg caattattta gtactgtcag tattgttata cgcacagata ttataacat   59

SEQ ID NO: 131          moltype = DNA  length = 59
FEATURE                 Location/Qualifiers
source                  1..59
                        mol_type = other DNA
                        note = Primer 81
                        organism = synthetic construct
SEQUENCE: 131
gcaaatgcct attgtgcaga tgttataata tctgtgcgta taacaatact gacagtact   59

SEQ ID NO: 132          moltype = DNA  length = 39
FEATURE                 Location/Qualifiers
source                  1..39
                        mol_type = other DNA
                        note = Primer 82
                        organism = synthetic construct
SEQUENCE: 132
cctgctcttc atgttttgaa tatgtattac ttggttatg                         39

SEQ ID NO: 133          moltype = DNA  length = 38
FEATURE                 Location/Qualifiers
source                  1..38
                        mol_type = other DNA
                        note = Primer 83
                        organism = synthetic construct
SEQUENCE: 133
cctgctcttc acatattgta atatgtgtgt ttgtttgg                          38

SEQ ID NO: 134          moltype = DNA  length = 59
FEATURE                 Location/Qualifiers
source                  1..59
                        mol_type = other DNA
                        note = Primer 84
                        organism = synthetic construct
SEQUENCE: 134
attatattat atgggtctgc aaggtagagg cgcgcttgtc acatgcagtg atgcacgcg   59

SEQ ID NO: 135          moltype = DNA  length = 59
FEATURE                 Location/Qualifiers
source                  1..59
                        mol_type = other DNA
                        note = Primer 85
                        organism = synthetic construct
SEQUENCE: 135
atgtaactta gcaccatcgc gcgtgcatca ctgcatgtga caagcgcgcc tctaccttg   59

SEQ ID NO: 136          moltype = DNA  length = 38
FEATURE                 Location/Qualifiers
source                  1..38
                        mol_type = other DNA
                        note = Primer 86
                        organism = synthetic construct
SEQUENCE: 136
cctgctcttc atgttgttaa ttcagtaaat tttcgatc                          38

SEQ ID NO: 137          moltype = DNA  length = 38
FEATURE                 Location/Qualifiers
source                  1..38
```

-continued

```
                        mol_type = other DNA
                        note = Primer 87
                        organism = synthetic construct
SEQUENCE: 137
cctgctcttc aggtttatgg cttgtatggg gcgaagac                 38

SEQ ID NO: 138          moltype = DNA  length = 37
FEATURE                 Location/Qualifiers
source                  1..37
                        mol_type = other DNA
                        note = Primer 88
                        organism = synthetic construct
SEQUENCE: 138
cctgctcttc agtaatgtct tctatcactt cttcttg                  37

SEQ ID NO: 139          moltype = DNA  length = 41
FEATURE                 Location/Qualifiers
source                  1..41
                        mol_type = other DNA
                        note = Primer 89
                        organism = synthetic construct
SEQUENCE: 139
cctgctcttc aacaatggct tctatcactg cttcttcttt c             41

SEQ ID NO: 140          moltype = DNA  length = 41
FEATURE                 Location/Qualifiers
source                  1..41
                        mol_type = other DNA
                        note = Primer 90
                        organism = synthetic construct
SEQUENCE: 140
cctgctcttc agatttaaca cttcttagca accaagtctt c             41

SEQ ID NO: 141          moltype = DNA  length = 37
FEATURE                 Location/Qualifiers
source                  1..37
                        mol_type = other DNA
                        note = Primer 91
                        organism = synthetic construct
SEQUENCE: 141
cctgctcttc aggtttagat tctagatggc ttctttc                  37

SEQ ID NO: 142          moltype = DNA  length = 38
FEATURE                 Location/Qualifiers
source                  1..38
                        mol_type = other DNA
                        note = Primer 92
                        organism = synthetic construct
SEQUENCE: 142
cctgctcttc agtaatgttg tctagaggtt ctttcttg                 38

SEQ ID NO: 143          moltype = DNA  length = 37
FEATURE                 Location/Qualifiers
source                  1..37
                        mol_type = other DNA
                        note = Primer 93
                        organism = synthetic construct
SEQUENCE: 143
cctgctcttc aacaatggct ttcgctttgc catcttc                  37

SEQ ID NO: 144          moltype = DNA  length = 38
FEATURE                 Location/Qualifiers
source                  1..38
                        mol_type = other DNA
                        note = Primer 94
                        organism = synthetic construct
SEQUENCE: 144
cctgctcttc agatttaagc gatgaattca accaattc                 38
```

ENGINEERED *SACCHAROMYCES CEREVISIAE* STRAINS FOR PRODUCTION OF VANILLYLAMINE AND CAPSAICIN, AND CONSTRUCTION METHOD AND USE THEREOF

CROSS REFERENCE TO RELATED APPLICATION

The present application is a continuation application of International Patent Application No. PCT/CN2023/086755, filed on Apr. 7, 2023, which claims priority to the Chinese Patent Application No. 202310194657.5, filed with the China National Intellectual Property Administration (CNIPA) on Mar. 1, 2023, and entitled "ENGINEERING *Saccharomyces cerevisiae* FOR PRODUCTION OF VANILLYLAMINE AND CAPSAICIN, AND CONSTRUCTION METHOD AND USE THEREOF", which is incorporated herein by reference in its entirety.

REFERENCE TO SEQUENCE LISTING

A computer readable XML file entitled "Sequence Listing", that was created on Oct. 30, 2023, with a file size of 193,606 bytes, contains the sequence listing for this application, has been filed with this application, and is hereby incorporated by reference in its entirety.

TECHNICAL FIELD

The present disclosure belongs to the technical field of bioengineering, and in particular relates to engineered *Saccharomyces cerevisiae* strains for production of vanillylamine and capsaicin, and a construction method and use thereof.

BACKGROUND

As an indispensable bulk chemical in the chemical industry, primary benzylamine plays an important role in the production of biological compounds, personal care products, and polymers synthesis. Vanillylamine, also known as 3-methoxy-4-hydroxy benzylamine, belongs to a type of classic primary benzylamines and is a precursor for the synthesis of bioactive compounds and the production of polyepoxides. The latest research shows that the vanillylamine has great advantages in the field of thrombolytic drug research. In plants, vanillylamine and 8-methyl-6-nonenoic acid are esterified under the catalysis of capsaicin synthase to generate capsaicin. As a synthetic active alkaloid in capsicum, capsaicin is widely used in food, drugs and other fields due to its significant anti-inflammatory and antibacterial activities. Due to special irritating characteristics, capsaicin is also used in the production of military products such as tear gas bombs. The simultaneous use of capsaicin and morphine drugs can reduce the addiction to morphine drugs. At present, the acquisition of capsaicin mainly depends on extracting from capsicum. However, due to a low content in plants and a large number of structural analogues for capsaicin, the subsequent separation and purification of capsaicin has become a great challenge. At present, vanillylamine can be produced by amination with precious metals as a catalyst and petrochemical products as a reaction substrate. However, this process is inconsistent with the requirements advocated by the green chemical industry. Studies have shown that genetically engineering *Escherichia coli* can produce vanillylamine using vanillic acid and ferulic acid in a lignin hydrolyzate as substrates, with a substrate conversion rate of up to 95%. However, this method is mainly limited by the concentration of products such as vanillic acid and ferulic acid in the lignin hydrolyzate, and yields up to 2.5 g/L. Moreover, a method for biosynthesizing capsaicin has not been previously reported.

SUMMARY

In view of this, an objective of the present disclosure is to provide engineered *Saccharomyces cerevisiae* strains for high production of vanillylamine and capsaicin.

To achieve the above objective, the present disclosure provides the following technical solutions:

The present disclosure provides an engineered *Saccharomyces cerevisiae* strain for production of vanillylamine, where two gene modules are inserted into the *Saccharomyces cerevisiae* genome: a gene module 1 includes PAL2, C4H, 4CL2, and HCT genes, and a gene module 2 includes CCoAoMT1, FerB2, and pAMT genes.

In the present disclosure, in order to realize the efficient assembly of a biosynthetic pathway of producing vanillylamine in *Saccharomyces cerevisiae* (*S. cerevisiae*), the pathway is divided into two modules. Module 1: starting with phenylalanine, through four-step enzyme catalysis using phenylalanine lyase (PAL), cinnamic acid-4-hydroxy lase (C4H), 4-coumaroyl-CoA ligase (4CL), and hydroxyl cinnamoyltransferase (HCT), caffeoyl-CoA is obtained. Module 2: using the caffeoyl-CoA as a substrate, the vanillylamine is obtained by catalysis with caffeic acid trans-methoxylase (CAMT), feruloyl-CoA lyase (FerB), and putative aminotransferase (pAMT). The modules I and II are constructed on the genome of *Saccharomyces cerevisiae* to realize the green fermentation and production of vanillylamine. The pattern diagram is shown in FIG. 1. Thus, the assembly of heterologous long pathways is easily and efficiently achieved in a modular method.

The present disclosure further provides a method of producing the engineered *Saccharomyces cerevisiae* strain, including the following steps: constructing two double transformation units of TPI1t-PAL2-TDH3p-ADH1p-C4H-PGI1t and ADH1t-4CL2-PGK1p-TEF2p-HCT-CYC1t: inserting the two double transformation units into a YPRCΔ15 site of a genome of *Saccharomyces cerevisiae* to obtain a strain Z1: constructing a gene expression cassette FBA1p-pAMT-ATP15t and a third double transformation unit HOG1t-CCoAoMT1-ENO2p-PYK1p-FerB2-LRP1t; and inserting the gene expression cassette and the third double transformation unit jointly into a YORWΔ17 site of a genome of the strain Z1.

The present disclosure further provides an engineered *Saccharomyces cerevisiae* strain for production of vanillylamine, where the engineered *Saccharomyces cerevisiae* is obtained by inserting pheA, Aro9, and TAL genes into the genome of the engineered *Saccharomyces cerevisiae* strain above. By overexpressing the shikimic acid pathway, the supply of precursors for the synthesis of vanillylamine is optimized, such that the production of vanillylamine in the engineered *Saccharomyces cerevisiae* is further improved. A method of producing vanillylamine includes the following steps: constructing two gene expression cassettes of PFY1p-pheA-PRC1t-ACT1p-Aro9-BAN4t and HXT7p-TAL-PRS28At; and inserting the two gene expression cassettes into a delta1 site of a genome of the engineered *Saccharomyces cerevisiae* strain.

The present disclosure further provides an engineered *Saccharomyces cerevisiae* for production of vanillylamine, where the engineered *Saccharomyces cerevisiae* strain is obtained by inserting SahH and SAM2 genes into the genome of any one of the engineered *Saccharomyces cerevisiae* strains above: alternatively, an engineered *Saccharomyces cerevisiae* strain is produced by inserting mtn, luxS, and SAM2 genes into the genome of any one of the engineered *Saccharomyces cerevisiae* strains above. In the present disclosure, the efficiency of methylation reactions involved in the synthetic pathway is improved by optimizing a regeneration ability of S-adenosyl-L-methionine (SAM). In this way, a fermentation yield of vanillylamine up to 16.48 g/L, which is the highest level of de novo biosynthesis of vanillylamine by *Saccharomyces cerevisiae*.

The present disclosure further provides a method for producing engineered *Saccharomyces cerevisiae* strains, including the following steps: constructing two gene expression cassettes of HIS-CYC1P-SahH-ALY2t and ENO2p-SAM2-SCW4t, and inserting the two gene expression cassettes into an rDNA site of a genome of any one of the engineered *Saccharomyces cerevisiae* strains above: alternatively; constructing two gene expression cassettes of HIS-FBA1p-mtn-NAT5t-ADH1p-luxS-IDP1t and ENO2p-SAM2-SCW4t, and inserting the two gene expression cassettes into an rDNA site of a genome of any one of the engineered *Saccharomyces cerevisiae* strains above.

The present disclosure further provides an engineered *Saccharomyces cerevisiae* strain for production of capsaicin, where the engineered *Saccharomyces cerevisiae* strain is produced by inserting Kas, Acl, Fat, and AT3 genes into any one of the engineered *Saccharomyces cerevisiae* strains above. In the present disclosure, a fatty acid branched pathway and capsaicin synthase related to capsaicin synthesis are further expressed in the engineered strains producing vanillylamine, thereby realizing the de novo biosynthesis of capsaicin. The pattern diagram is shown in FIG. 1. As shown in FIG. 1, the synthetic pathway of vanillylamine and its derivative capsaicin are divided into three modules. The three modules are constructed on the genome of *Saccharomyces cerevisiae*, so as to realize the de novo biosynthesis of vanillylamine and capsaicin. The present disclosure is the first time to produce capsaicin de novo by engineered *Saccharomyces cerevisiae* strains. The present disclosure further provides a method of producing the engineered *Saccharomyces cerevisiae* strains, including the following steps: constructing two double transformation units of ASP3t-Kas-PGK1p-FBA1p-Acl-HAP4t and YCP4t-Fat-GPM1p-ACT1p-AT3-MDM35t, and constructing the two double transformation units into a YORWΔ22 site of a genome of any one of the engineered *Saccharomyces cerevisiae* strains.

The present disclosure further provides use of any one of the engineered *Saccharomyces cerevisiae* strains in production of vanillylamine.

The present disclosure further provides use of any one of the engineered *Saccharomyces cerevisiae* strains in production of capsaicin.

The present disclosure has the following beneficial effects:

In the present disclosure, a synthesis pathway of vanillylamine is expressed heterologously in engineered *Saccharomyces cerevisiae* strains for the first time, and biosynthesis of the vanillylamine is realized for the first time. After the optimization of precursors supply and the optimization of S-adenosyl-L-methionine (SAM) cycle, a yield of the vanillylamine reaches 16.48 g/L, and a synthesis efficiency of the vanillylamine is increased by nearly 150%. This is the highest optimization efficiency obtained by optimizing a SAM cofactor strategy so far.

Based on the synthesis of vanillylamine by the engineered *Saccharomyces cerevisiae* strains, a synthesis pathway of 8-methyl-6-nonenoyl-coenzyme A is constructed heterologously, and a capsaicin synthase AT3 is expressed heterologously. In this way, de novo total biosynthesis of the capsaicin is realized for the first time, and a yield of the capsaicin is 80.23 μg/L.

In the present disclosure, the engineered *Saccharomyces cerevisiae* strains directly generate vanillylamine and capsaicin by glucose metabolism, which has enabled the de novo biosynthesis of the bulk chemical vanillylamine, and its complex derivative capsaicin. These engineered strains use a constitutive promoter and a strong terminator to control the high-level expression of heterologous genes, without adding inducers or additional high-priced substrates. In this way, a fermentation process is simplified, a production cost is reduced, and the vanillylamine and capsaicin can be biosynthesized by direct fermentation, compared with chemical synthesis, this technology is more in line with the concept of green and sustainable development.

BRIEF DESCRIPTION OF THE DRAWINGS

FIG. 3A shows the HPLC-MS/MS diagram of a capsaicin standard sample, and FIG. 3B shows the HPLC-MS/MS diagram of capsaicin synthesized by an engineered yeast strain.

DETAILED DESCRIPTION OF THE EMBODIMENTS

Figure 1:
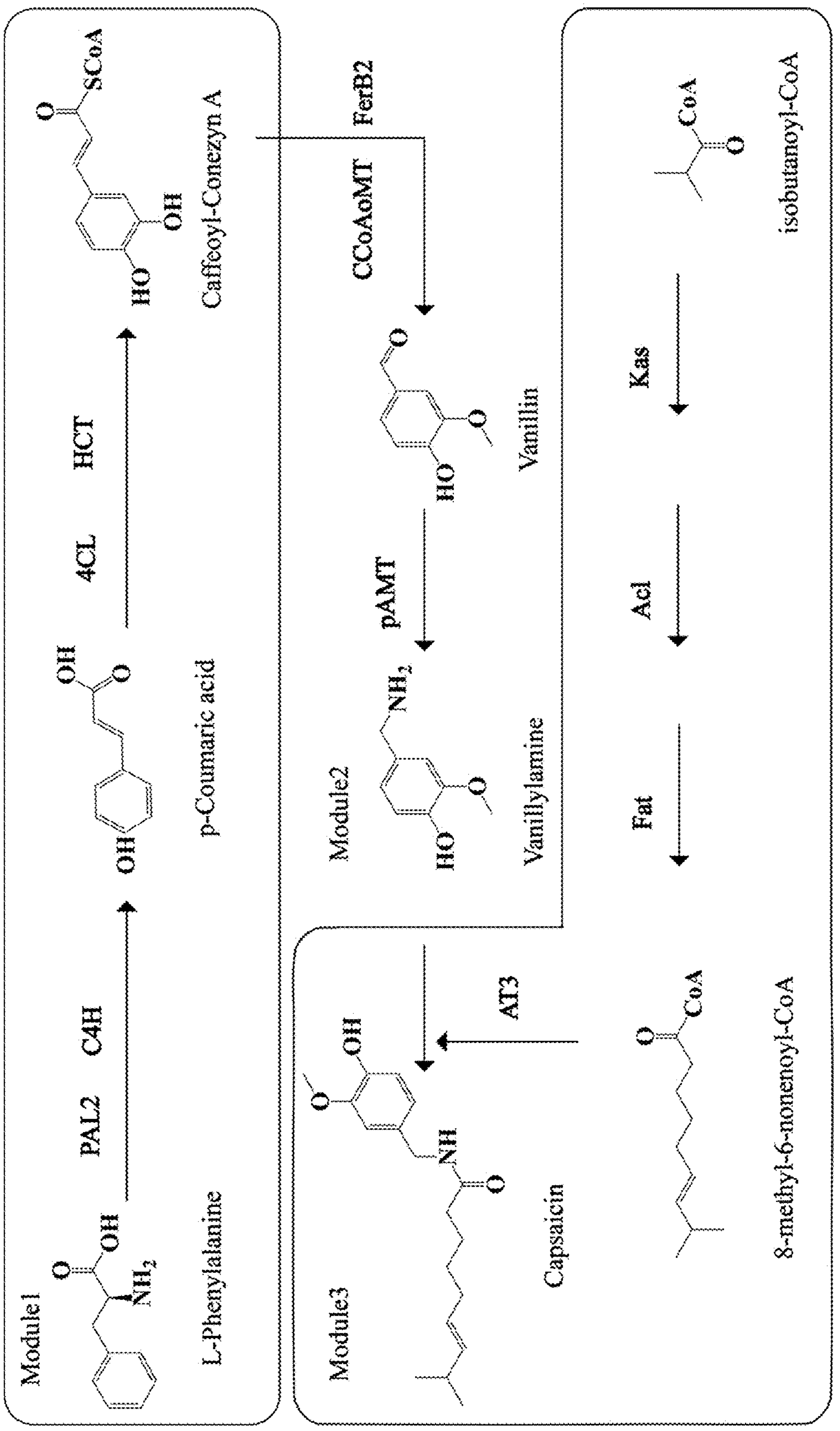
FIG. 1 shows a hierarchical design schema diagram of the approaches for vanillylamine and capsaicin.

The technical solution provided by the present disclosure will be described in detail below with reference to examples, which should not be construed as limiting the protection scope of the present disclosure.

In the following examples, all methods are conventional methods unless otherwise specified.

All materials and reagents used in the following examples may be commercially available unless otherwise specified.

Example 1

Construction of engineered *Saccharomyces cerevisiae* strain for vanillylamine synthesis 1) PAL2, C4H, and 4CL2 genes from *Arabidopsis*, HCT and CCoAoMT1 genes from tobacco, a FerB2 gene from *Sphingomonas*, and a pAMT gene from pepper were selected. The coding genes of the above-mentioned genes were codon-optimized and chemically synthesized by GENEWIZ Company. The synthesized PAL2 had a nucleotide sequence shown in SEQ ID NO: 1, the C4H had a nucleotide sequence shown in SEQ ID NO: 2, the 4CL2 had a nucleotide sequence shown in SEQ ID NO: 3, the HCT had a nucleotide sequence shown in SEQ ID NO: 4, the CCoAoMT1 had a nucleotide sequence shown in SEQ ID NO: 5, the FerB2 had a nucleotide sequence shown in SEQ ID NO: 6, and the pAMT had a nucleotide sequence shown in Shown in SEQ ID NO: 7.

2) The constitutive promoters TDH3p, ADH1p, PGK1p, and TEF2p in *Saccharomyces cerevisiae* were selected, and two head-to-head promoter modules were constructed with a genome of *Saccharomyces cerevisiae* as a template by OE-PCR using the primer sequences 1 to 8. The two promoter modules were saved into a plasmid. A specific process was as follows:

a: A reaction system included: 60 ng of purified and recovered fragments of TDH3p, 60 ng of purified and recovered fragments of ADH1p, 2 μL of dNTP (10 mM), 1 μL of PrimeSTAR DNA polymerase, 10 μL of 5×PrimeSTAR Buffer, and add water to make up to 50 μL; PCR was conducted by a PCR instrument: 98° C. for 3 min; 98° C. for 10 s, 65° C. for 1 min (1 Kb/min), cycled 30 times; 68° C. for 5 min, and stored at 4° C. b: After the reaction, Tiangen's Pfu DNA polymerase was used, the above-mentioned reaction solution without purification was used as a template, and conventional PCR amplification was conducted with primers 1 and 4 to obtain a TDH3p+ADH1p-connected fragment. c: After purification and recovery, 50 ng of the TDH3p+ADH1p fragment was selected (the amount was determined by a length of the gene fragment, 50 ng/Kb), 1 μL of pBM16A Vevtor and 1 μL of 10×Toposmart were added (the reagent was a pBM16A Toposmart cloning kit was purchased from Biomed Company) box), and water was added to make up to 10 μL; a resulting system was mixed evenly, and PCR was conducted at 25° C. for 30 min. d: After the reaction, 10 μL of an obtained reaction solution was added to 100 μL of *Escherichia coli* competent cells melted on ice, mixed gently, and kept in ice bath for 30 min. e: After the cells were heat-shocked at 42° C. for 90 s, they were immediately transferred to ice water for 2 min. f: 900 μL of LB medium was added to the competent cells, and cultured with shaking at 200 rpm for 1 h at 37° C. g: Centrifugation was conducted at 4000 rpm for 1 min, 900 μL of supernatant was removed, the cells were resuspended with the remaining liquid, spread evenly on an LB plate containing 100 μg/L Amp, cultured overnight at 37° C., colony PCR was conducted to verify correct single colony, and a plasmid was extracted from the correct single colony and then sent to GENEWIZ for sequencing. In this way, the TDH3p+ADH1p fragment was stored in a plasmid pBM16A for later use (pBM16A-TDH3p+ADH1p); steps a to g were repeated to save a prepared spare plasmid pBM16A-PGK1p+TEF2p.

3) TPI1t, PGI1t, ADH1t, and CYC1t were assembled into two back-to-back terminator modules (a Sap1 restriction site was inserted between the two terminators and homology arms L1-L2, L3-L4 were added at both ends). The functional genes were amplified by PCR using primers 9 to 16 (the functional genes were all based on the plasmid synthesized by entrusting GENEWIZ as a template), and the Sap1 restriction sites corresponding to the promoter module and the terminator module were assembled at both ends.

The primer sequences involved in the above process included:

Primer 1: 5'>CCTGCTCTTCACATTTTGTTTATGTGTGTTTATTC<3' (SEQ ID NO: 51), the upstream primer for the amplification of promoter TDH3p, the underlined sequence was a cohesive end formed after the promoter TDH3p was digested by Sap1.

Primer 2: 5'>TCTGTTCTATTGTATATCTCCCCTCCGCCACCTACATGTATAC TAGCGTTGAATGTTAG<3' (SEQ ID NO: 52), the promoter TDH3p for the amplification of downstream primer, the underlined sequence was an overlapping sequence with the promoter ADH1p.

Primer 3: 5'>AAACTTCTTGTTGTTGACGCTAACATTCAACGCTAGTATAC ATGTAGGTGGCGGAGGGG<3' (SEQ ID NO: 53), the upstream primer for the amplification of promoter ADH1p, the underlined sequence was an overlapping sequence with the promoter TDH3p.

Primer 4: 5'>CCTGCTCTTCATGTATATGAGATAGTTGATTGTATG<3' (SEQ ID NO: 54), the downstream primer for the amplification of promoter ADH1p, the underlined sequence was a cohesive end formed after the promoter ADH1p was digested by Sap1.

Primer 5: 5'>CCTGCTCTTCACATTGTTTTATATTTGTTGTAAAAAG<3' (SEQ ID NO: 55), the upstream primer for the amplification of promoter PGK1p, the underlined sequence was a cohesive end formed after the promoter PGK1p was digested by Sap1.

Primer 6: 5'>GGAAGCGCCTACGCTTGACATCTACTATATGTAAGTATAAC GCACAGATATTATAACAT<3' (SEQ ID NO: 56), the downstream primer for the amplification of promoter PGK1p, the underlined sequence was an overlapping sequence with the promoter TEF2p.

Primer 7: 5'>GCAAATGCCTATTGTGCAGATGTTATAATATCTGTGCGTTA TACTTACATATAGTAGAT<3' (SEQ ID NO: 57), the upstream primer for the amplification of promoter TEF2p, the underlined sequence was an overlapping sequence with the promoter PGK1p.

Primer 8: 5'>CCTGCTCTTCATGTGGTACTAGTGTTTAGTTAATTATAG<3' (SEQ ID NO: 58), the downstream primer for the amplification of promoter TEF2p, the underlined sequence was a cohesive end of promoter TEF2p after Sap1 digestion.

Primer 9: 5'>CCTGCTCTTCAGGTTTAACAAATTGGAATAGGAGCACCGT TC<3' (SEQ ID NO: 59), the upstream primer for gene PAL2 amplification, the underlined sequence was a cohesive end of gene PAL2 after Sap1 digestion.

Primer 10: 5'>CCTGCTCTTCAGTAATGGACCAAATTGAGGCAATGTTG<3' (SEQ ID NO: 60), the downstream primer for gene PAL2 amplification, the underlined sequence was a cohesive end of gene PAL2 after Sap1 digestion.

Primer 11: 5'>CCTGCTCTTCAACA ATGGACTTGTTGTTGTTGGAAAAG<3' (SEQ ID NO: 61), the upstream primer for gene C4H amplification, the underlined sequence was a cohesive end of gene C4H after Sap1 digestion.

Primer 12: 5'>CCTGCTCTTCAGATTTAACAATTTCTTGGCTTCATAAC<3' (SEQ ID NO: 62), downstream primers for gene C4H amplification, the underlined sequence was a cohesive end of gene C4H after Sap1 digestion.

Primer 13: 5'>CCTGCTCTTCAGGT TTAACATAACTTAGCTTTTAAATC<3' (SEQ ID NO: 63), the upstream primer for gene 4CL2 amplification, the underlined sequence was a cohesive end of gene 4CL2 after Sap1 digestion.

Primer 14: 5'>CCTGCTCTTCAGTAATGAT-TACTGCAGCATTGCACG<3' (SEQ ID NO: 64), downstream primer for gene 4CL2 amplification, the underlined sequence was a cohesive end of gene 4CL2 after Sap1 digestion.

Primer 15: 5'>CCTGCTCTTCAACAATGAAAATT-GAAGTTAAAGAATC<3' (SEQ ID NO: 65), the upstream primer for gene HCT amplification, the underlined sequence was a cohesive end of gene HCT after Sap1 digestion.

Primer 16: 5'>CCTGCTCTTCAGAT TTAAAAATCGTACAAAAATTTCTCA AAC<3' (SEQ ID NO: 66), the downstream primer for HCT amplification, the underlined sequence is the cohesive end of gene HCT after Sap1 digestion.

4) Using a Golden Gate ligation method, and using a terminator module as a receiving plasmid (0.2 pmol), the promoter module and two functional genes (each 0.6 pmol) were inserted. The Golden Gate included:

The reaction was completed in a 10 μL system, including: 2.5 μL Anza T4 DNA Ligase Master Mix, 0.5 μL Anza10× Buffer, 0.2 pmol acceptor vector, inserted fragment 0.6 pmol, 0.5 μL Anza 36 Eco31l, and adding sterile water to make up to 10 μL. All enzymes were purchased from Thermo Fisher. The Golden Gate reaction was conducted in a PCR instrument: 37° C. for 5 min; 37° C. for 1 min, 23° C. for 1 min, 30 cycles of reaction; 37° C. for 5 min; 65° C. for 10 min; stored at 4° C. 10 μL of the assembly mixture was transformed into *E. coli* DH5α competent cells and incubated overnight at 37° C. on an LB agar plate with Amp antibiotics. 50 colonies were randomly selected from the LB agar plate with 2×Taq Master Mix (TIANGEN) for PCR verification, and correct colonies were selected. Two double transformation units DH5α/PUC57T-(TPI1t-PAL2-TDH3p-ADH1p-C4H-PGI1t) and DH5α/PUC57T-(ADH1t-4CL2-PGK1p-TEF2p-HCT-CYC1t) were assembled by the above method.

5) According to the following steps, the two double transformation units (obtained in step 4) containing PAL2, C4H, HCT, and 4CL2 were inserted into a YPRCΔ15 site of the genome of *Saccharomyces cerevisiae* to realize the assembly of module 1 to form a strain Z1:

a. Preparation of Competent Cells of *Saccharomyces cerevisiae*

(1) A single clone was selected on a solid plate, transferred to a YPD liquid medium without antibiotics, and cultured overnight in a shaker at 30° C. and 200 rpm. (2) The cultured bacterial solution was transferred to a fresh YPD liquid medium without antibiotics at a volume of 10%, and continued to culture in a shaker at 30° C. and 200 rpm for 5-8 h. (3) 1.5 ml of the bacterial solution was placed in a centrifuge tube, centrifuged at 5000 rpm for 3 min, and a supernatant was discarded. (4) The cells were resuspended in 1 ml of sterile water, centrifuged at 5000 rpm for 2 min, and a supernatant was discarded. (5) The cells were resuspended with 1 mL of 100 mM LiAc, allowed to stand for 3 min, centrifuged at 4000 rpm for 4 min, 900 μl of the supernatant was discarded, the cells were resuspended, and placed on ice. The *Saccharomyces cerevisiae* competent cells were prepared.

b. Transformation of *Saccharomyces Cerevisiae*

(1) 40 μL of 10% salmon sperm single-stranded ssDNA was denatured in boiling water for 5 min, and immediately inserted into ice for later use. (2) 500 ng for each of the two double transformation units prepared in 4) were added to a new centrifuge tube, 500 ng of the plasmid (Δ15 site1) containing the upper end sequence of the YPRC Δ15 site and the selection marker gene, and the plasmid (Δ15 site2) containing the upper end sequence of the YPRC Δ15 site were added with 40 uL of denatured 10% salmon sperm single-stranded ssDNA. A mixture of the above two was transferred to *S. cerevisiae* competent cells placed on ice, and 50% w/v PEG 3350 480 μL and 1 M LiAc 72 μL were added sequentially. The centrifuge tube was vortexed at high speed for 1 min to fully mix the components. (3) A transformation system was put in a 30° C. incubator and allowed to stand for 30 min. (4) 72 μL dimethyl sulfoxide (DMSO) was added, and vortexed to mix well. (5) The centrifuge tube was placed in a 42° C. water bath, heat-shocked for 10 min, centrifuged at 4000 rpm for 5 min, and a supernatant was discarded. (6) 200 μL of 5 mM $CaCl_2$ was added, the cells were resuspended and mixed well, allowed to stand for 10 min, centrifuged at 4000 rpm for 5 min, and a supernatant was discarded. (7) 1 mL of sterile water was added to resuspend and wash the cells, centrifuged at 4000 rpm for 1 min, a supernatant was discarded; then 100 uL of sterile water was added to resuspend the cells, and applied to the corresponding solid medium. (8) inverted culture was conducted in a constant-temperature incubator at 30° C. for 2-4 d.

6) On the basis of the strain Z1, the three coding genes CCoAoMT1, FerB2, and pAMT were constructed into a YORWΔ17 site of the genome of *Saccharomyces cerevisiae* by the method of 5). In this way, the assembly of module 2 in *Saccharomyces cerevisiae* was realized, and a final engineered *Saccharomyces cerevisiae* strain (Z2) was generated. In this step, ENO2p, PYK1p, FBA1p promoters and HOG1t, LRP1t, ATP15t terminators were selected to control gene expression. Since there were only three genes in this module, pAMT directly followed the OE-PCR method in step 2) to assemble the pAMT gene expression cassette: FBA1p-pAMT-ATP15t. A double transformation unit of CCoAoMT1 and FerB2 was constructed by the method in step 4): HOG1t-CCoAoMT1-ENO2p-PYK1p-FerB2-LRP1t.

The gene sequence of strain Z2 constructed by the above method was based on the YORWΔ15 site in the genome of *Saccharomyces cerevisiae*: URA3-TPIt-PAL2-TDH3p-ADH1p-C4H-PGI1t-ADH1t-4CL2-PGKp-TEF2p-HCT-CYC1t;

YORWΔ17 site was: TEF1p-hphNT1-CYC1t-HOG1t-CCoAoMT1-ENO2p-PYK1p-FerB2-LRP1t-FBA1p-pAMT-ATP15t.

In step 6), the primer sequences involved were as follows:

Primer 17: 5'>CCTGCTCTTCACATGGTCTCACATCT-ATTATTGTATG<3' (SEQ ID NO: 67), the upstream primer for the amplification of promoter ENO2p, the underlined sequence was a cohesive end formed after the promoter ENO2p was digested by Sap1.

Primer 18: 5'>TTGTACAT-ACTAATATATATAAACAAAGTAACGTCTCCT ACGCGGCGTTATGTCACTAA<3' (SEQ ID NO: 68), the downstream primer for amplification of promoter ENO2p, the underlined sequence was an overlapping sequence with the promoter PYK1p.

Primer 19: 5'>CGCAAGTTGGTGCACGTCGTTAGTGACATAACGCCGCGT AGGAGACGTTACTTTGTTTA<3' (SEQ ID NO: 69), the upstream primer for the amplification of the promoter PYK1p, the underlined sequence is the overlapping sequence with the promoter ENO2p.

Primer 20: 5'>CCTGCTCTTCATGTATAATTTGCGATCGTAGTTGGG<3' (SEQ ID NO: 70), the downstream primer for the amplification of promoter PYK1p, the underlined sequence was a cohesive end formed after the promoter PYK1p was digested by Sap1.

Primer 21: 5'>CCTGCTCTTCAGGT TTAAGATATTCTTCTGCACAAAG<3' (SEQ ID NO: 71), the upstream primer for gene CCoAoMT1 amplification, the underlined sequence was a cohesive end of gene CCoAoMT1 after Sap1 digestion.

Primer 22: 5'>CCTGCTCTTCAGTAATGGCTACTAACGGTAGACACCAAG<3' (SEQ ID NO: 72), the downstream primer for gene CCoAoMT1 amplification, the underlined sequence was a cohesive end of gene CCoAoMT1 after Sap1 digestion.

Primer 23: 5'>CCTGCTCTTCAACA ATGTCTGATGAATTGACATTTG<3' (SEQ ID NO: 73), the upstream primer for gene FerB2 amplification, the underlined sequence was a cohesive end of gene FerB2 after Sap1 digestion.

Primer 24: 5'>CCTGCTCTTCAGATTTAATCTTCTCTTCTATAACCAC<3' (SEQ ID NO: 74), the downstream primer for gene FerB2 amplification, the underlined sequence was a cohesive end of gene FerB2 after Sap1 digestion.

Primer 25: 5'>CTTGTATTGTTCTAACGATCCGACCATTTCATCCTGAAT ATAACAATACTGACAGTACT<3' (SEQ ID NO: 75), the upstream primer for the amplification of the promoter FBA1p, the underlined sequence was an overlapping sequence with the terminator LRP1t.

Primer 26: 5'>CATATCATGACCCATAAATTCGTTTGTAATATTTGCCAT TTTGAATATGTATTACTTGG<3' (SEQ ID NO: 76), the downstream primer for the amplification of the promoter FBA1p, the underlined sequence was an overlapping sequence with the gene pAMT.

Primer 27: 5'>TTGTCATATATAACCATAACCAAGTAATACATATTCAAA ATGGCAAATATTACAAACGA<3' (SEQ ID NO: 77), the upstream primer for gene pAMT amplification, the underlined sequence was an overlapping sequence with the promoter FBA1p.

Primer 28: 5'>CGAGTAAAAAAAGAGCTGCAGTTCCCAGGAAGCGTTAAA TTATTGTTTTTGTGACTTCA<3' (SEQ ID NO: 78), the downstream primer for gene pAMT amplification, the underlined sequence is the overlapping sequence with the terminator AT915t.

Primer 29: 5'>GAAAAAAGAGTTGAAGAATTGAAGTCACAAAAACAATAA TTTAACGCTTCCTGGGAACT<3' (SEQ ID NO: 79), the upstream primer for the amplification of terminator ATP15t, the underlined sequence was an overlapping sequence with the gene pAMT.

Primer 30: 5'>GTGATGAATTTTGAGAGCCCACTTTTGTTGGGGACGATT GAGAGGCTGAAGGCAGAGAA<3' (SEQ ID NO: 80), the downstream primer for the amplification of terminator ATP15t, the underlined sequence was an overlapping sequence with the YORWΔ17 site.

The nucleotide sequences of the promoter and terminator involved in the above process were: TDH3p (SEQ ID NO: 8), ADH1p (SEQ ID NO: 9), PGK1p (SEQ ID NO: 10), TEF2p (SEQ ID NO: 11), TPI1t (SEQ ID NO: 12), PGI1t (SEQ ID NO: 13), ADH1t (SEQ ID NO: 14), CYC1t (SEQ ID NO: 15), ENO2p (SEQ ID NO: 16), PYK1p (SEQ ID NO: 17), FBA1p (SEQ ID NO: 18), HOG1t (SEQ ID NO: 19), LRP1t (SEQ ID NO: 20), ATP15t (SEQ ID NO: 21).

7) Z2 strain fermentation test: a single colony verified by PCR was selected from the plate, and inoculated into 20 mL of YPD medium (2% glucose, 2% peptone, 1% yeast powder), cultured at 220 rpm and 30° C. for 36 h to obtain a seed solution. The seed solution was inoculated into a 1 L fermenter with 600 mL of medium at an inoculation amount of the initial $OD_{600}$ value of 0.1, and then cultured at a pH value of 7.0 and 30° C. under a ventilation flow at 0.1 and a rotational speed at 170 rpm for 96 h. 24 h after inoculation, 6 g of glucose was supplemented every 12 h until the end of fermentation, and samples were taken every 24 h. 1 mL of 1 M HCl was added into 5 mL of a fermentation broth, heated to boil for 10 min to fully lyse the bacterial cells. Centrifugation was conducted to remove bacterial cells, 1 mL of supernatant was added with an equal volume of methanol to remove salt, and then subjected to HPLC for qualitative and quantitative analysis to determine the content of vanillylamine. The results showed that the content of vanillylamine reached 6.47 g/L after the fermentation of engineered *Saccharomyces cerevisiae* strain.

Example 2

Modification of yeast intrinsic pathway to enhance vanillylamine production

1) The coding gene pheA (nucleotide sequence shown in SEQ ID NO: 22) of bifunctional chorismate mutase prebenzoate dehydratase derived from *E. coli* and the transaminase coding gene Aro9 of *Saccharomyces cerevisiae* (nucleotide sequence shown in SEQ ID NO: 23), and the PFY1p promoter (nucleotide sequence shown in SEQ ID NO: 24), ACT1p promoter (nucleotide sequence shown in SEQ ID NO: 25), as well as the PRC1t terminator (nucleotide sequence shown in SEQ ID NO: 26), and BAN4t terminator (nucleotide sequence shown in SEQ ID NO: 27) terminator were assembled into a gene expression cassette using the method of OE-PCR in Example 1: PFY1p-pheA-PRC1t-ACT1p-Aro9-BAN4t.

The primer sequences used in the above steps were as follows (both promoter and terminator used the genome of *Saccharomyces cerevisiae* as a template; the target gene pheA used the genome of *E. coli* MG1655 as a template; the target gene Aro9 used the genome of *Saccharomyces cerevisiae* as a template):

Primer 31: 5'>GCATCCACATCTTCACATGAAAATAGAGGCCAATCAGGC AGGAGACGTTACTTTGTTTA<3' (SEQ ID NO: 81), the upstream primer for the amplification of promoter PFY1p, the underlined sequence was an overlapping sequence with the terminator PRS28At.

Primer 32: 5'>TTTCTCTCGCAGCGCCAGTAACGGGTTTTCCGATGTCAT ATAATTTGCGATCGTAGTTG<3' (SEQ ID NO: 82), the downstream primer for the amplification of the promoter PFY1p, the underlined sequence was an overlapping sequence with the gene pheA.

Primer 33: 5'>TACATACACAACATAAACCCAACTACGATCGCAAATTAT ATGACATCGGAAAACCCGTT<3' (SEQ ID NO: 83), the upstream primer for gene pheA amplification, the underlined sequence was an overlapping sequence with the promoter FBA1p.

Primer 34: 5'>CTGATAATAAAAACGGTATGCCTACACATACACGCTTTA TCAGGTTGGATCAACAGGCA<3' (SEQ ID NO: 84), the downstream primer for gene pheA amplification, the underlined sequence was an overlapping sequence with the terminator PRC1t.

Primer 35: 5'>TACCCAAGTGAGAACGTAGTGCCTGTTGATCCAACCTGA TAAAGCGTGTATGTGTAGGC<3' (SEQ ID NO: 85), the upstream primer for amplification of the terminator PRC1t, the underlined sequence was an overlapping sequence with the gene pheA.

Primer 36: 5'>ATTATATTATATGGGTCTGCAAGGTAGAGGCGCGCTTGT GCAGCGATCAGCAATAATGA<3' (SEQ ID NO: 86), downstream primer for terminator PRC1t amplification, the underlined sequence was an overlapping sequence with the promoter ACT1p.

Primer 37: 5'>ATTCCGCGTTTGCTTCATTTCATTATTGCTGATCGCTGC ACAAGCGCGCCTCTACCTTG<3' (SEQ ID NO: 87), the upstream primer for the amplification of promoter ACT1p, the underlined sequence was an overlapping sequence with the terminator PRC1t.

Primer 38: 5'>GGAAGTGTAATCAACAGGGGGGGCAGAACCAGCAGTCAT TGTTAATTCAGTAAATTTTC<3' (SEQ ID NO: 88), the downstream primer for the amplification of promoter ACT1p, the underlined sequence was an overlapping sequence with gene aro9.

Primer 39: 5'>CTTTTTTCTTCCCAAGATCGAAAATTTACTGAATTAACA ATGACTGCTGGTTCTGCCCC<3' (SEQ ID NO: 89), the upstream primer for gene aro9 amplification, the underlined sequence was an overlapping sequence with the promoter ACT1p.

Primer 40: 5'>CCTCTCCTAGCGTACACGGATGGCAAGAATAAACTGGCT TCAACTTTTATAGTTGTCAA<3' (SEQ ID NO: 90), the downstream primer for gene aro9 amplification, the underlined sequence was an overlapping sequence with the terminator BNA4t.

Primer 41: 5'>AGTGGCATAAAAGAATTTTTTGACAACTATAAAAGTTGA AGCCAGTTTATTCTTGCCAT<3' (SEQ ID NO: 91), the upstream primer for amplification of the terminator BNA4t, the underlined sequence was an overlapping sequence with the gene pheA.

Primer 42: 5'>AGCTGAAATGCAAGGATTGATAAAATAATAGGATAATA GAAGAATGGATCAAAATGGC<3' (SEQ ID NO: 92), the downstream primer for amplification of the terminator PRC1t, the underlined sequence was an overlapping sequence with the delta1 site.

2) The coding gene TAL (nucleotide sequence shown in SEQ ID NO: 28) of tyrosine lyase derived from *Arabidopsis thaliana*, and the promoter HXT7p (nucleotide sequence shown in SEQ ID NO: 29) and the terminator PRS28At (nucleotide sequence shown in SEQ ID NO: 30) were assembled into a gene expression cassette HXT7p-TAL-PRS28At using the OE-PCR method in Example 1. The obtained gene expression cassette and the gene expression cassette assembled in step 1) were jointly constructed into the delta1 site of the genome of the strain Z2 obtained in Example 1 through lithium acetate transformation (same as step 5) in Example 1), to strengthen the precursor supply for synthesis of vanillylamine. The obtained engineered *Saccharomyces cerevisiae* strain was named Z3. The gene sequence of strain Z3 was based on the genome of *Saccharomyces cerevisiae:*

YORWΔ15:URA3-TPIt-PAL2-TDH3p-ADH1p-C4H-PGI1t-ADH1t-4CL2-PGKp-TEF2p-HCT-CYC1t

YORWΔ17:TEF1p-hphNT1-CYC1t-HOG1t-CCoA-oMT1-ENO2p-PYK1p-FerB2-LRP1t-FBA1p-pAMT-ATP15t Delta1:LEU-HXT7p-TAL-PRS28At-PFY1p-pheA-PRC1t-HXT7p-Aro9-BAN4t.

The primer sequences involved in the above steps were as follows (both the promoter and the terminator used the genome of *Saccharomyces cerevisiae* as a template; the target gene TAL used a gene plasmid synthesized by entrusting GENEWIZ as a template; an LEU selection marker used an LEU selection marker plasmid purchased from BIOFENG as a template):

Primer 43: 5'>ATAACATCTTTTTTTATTCCTTCTTTGATATTTTGTCA aactgtgggaatactcaggt<3' (SEQ ID NO: 93), the upstream primer for LEU screening marker amplification, the underlined sequence was an overlapping sequence with the delta1 site.

Primer 44: 5'>AACACGCAGGGGCCCGAAATTGTTCCTACGAGAAGTAGT TGCTTACCTGTATTCCTTTA<3' (SEQ ID NO: 94), the downstream primer for LEU screening marker amplification, the underlined sequence was an overlapping sequence with the promoter HXT7p.

Primer 45: 5'>AGGAGAAAAAGGAGGATAGTAAAGGAATACAGGTAAGCA ACTACTTCTCGTAGGAACAA<3' (SEQ ID NO: 95), the upstream primer for the amplification of promoter HXT7p, the underlined sequence was an overlapping sequence with the LEU screening marker.

Primer 46: 5'>AGACAATCTGTCAGCTTGTCTTTCAACAACTTGAGTCAT TTTTTAATTTTAATCAAAAA<3' (SEQ ID NO: 96), the downstream primer for the amplification of the promoter HXT7p, the underlined sequence was an overlapping sequence with the gene TAL.

Primer 47: 5'>AACACAAAAACAAAAAGTTTTTTTAATTTTAATCAAAAA ATGACTCAAGTTGTTGAAAG<3' (SEQ ID NO: 97), the upstream primer for gene TAL amplification, the underlined sequence was an overlapping sequence with the promoter FBA1p.

Primer 48: 5'>TTTTGTATAGCTGCAACCTTCAATCTGCAAATAAGCTTC TTAACCGAAGTCCTTACCGT<3' (SEQ ID NO: 98), the downstream primer for gene TAL amplification, the underlined sequence was an overlapping sequence with the terminator PRS28At.

Primer 49: 5'>TTTGTTGGTTGACGAAGCTGACGGTAAGGACTTCGGTTAA GAAGCTTATTTGCAGATTGA<3' (SEQ ID NO: 99), the upstream primer for the amplification of the terminator PRS28At, the underlined sequence was an overlapping sequence with the gene TAL.

Primer 50: 5'>TTGTACATACTAATATATATAAACAAAGTAACGTCTCCT GCCTGATTGGCCTCTATTTT<3' (SEQ ID NO: 100), the downstream primer for amplification of the terminator PRS28At, the underlined sequence is the overlapping sequence with the promoter PFY1p.

3) The strain Z3 was fermented by the method of step 7) in Example 1, and the yield of vanillylamine increased to 7.16 g/L, which was 11% higher than that of the unoptimized strain.

Example 3

Reconstruction of the SAM cycle to optimize the synthesis of vanillylamine

1) In the present disclosure, in order to optimize the synthesis of vanillylamine, primers 51 and 52 were used to amplify the coding gene sahH of SAH hydrolase using the genome of *Saccharomyces cerevisiae* as a template (nucleotide sequence shown in SEQ ID NO: 31). Primer 53 and primer 54 were used to amplify the gene SAM2 (nucleotide sequence shown in SEQ ID NO: 32) encoding SAM synthase derived from *Arabidopsis thaliana*, and the gene was chemically synthesized by GENEWIZ after codon optimization.

The primer sequences involved were as follows:

Primer 51: 5'>TATAGACACACAAACACAAATACACACACTAAATTAATA ATGTCTGCTCCAGCTCAAAA<3' (SEQ ID NO: 101), the upstream primer for gene sahH amplification, the underlined sequence was an overlapping sequence with the promoter CYC1p.

Primer 52: 5'>TAAGAACAGGAAGGGATGACGTAGGAACCTTGTGCTAGA TCAATATCTGTAGTGGTCGG<3' (SEQ ID NO: 102), the downstream primer for gene sahH amplification, the underlined sequence was an overlapping sequence with the terminator ALY2t.

Primer 53: 5'>CATAACACCAAGCAACTAATACTATAACATACAATAATA ATGGAAACTTTCTTGTTCAC<3' (SEQ ID NO: 103), the upstream primer for gene SAM2 amplification, the underlined sequence was an overlapping sequence with the promoter ENO2p.

Primer 54: 5'>ATCAAGATTTTTTTGTTTTTTTTACAATTGAGTAGAC TTAAGCTTGTGGCTTGTCCC<3' (SEQ ID NO: 104), the downstream primer for gene SAM2 amplification, the underlined sequence was an overlapping sequence with the terminator SCW4t. (Taking a gene plasmid synthesized by entrusting GENEWIZ as a template)

2) The amplification was conducted with the following corresponding primers using the genome of *Saccharomyces cerevisiae* as a template, to obtain promoters: CYC1p (nucleotide sequence shown in SEQ ID NO: 33), ENO2p (nucleotide sequence shown in SEQ ID NO: 16); terminators: ALY2t (nucleotide sequence shown in SEQ ID NO: 34), SCW4t (nucleotide sequence shown in SEQ ID NO: 35). The primers 55 and 56, PCR-amplified HIS screening marker gene, and the gene fragments amplified in the above step were assembled into gene expression cassettes according to the processes a to b in step 3) of Example 1: HIS-CYC1p-sahH-ALY2t; ENO2p-SAM2-SCW4t. The two gene expression cassettes were constructed into the rDNA sites of the genomes of strains Z2 and Z3 by the transformation method in 5) in Example 1 to form strains Z4 and Z7, respectively.

The gene sequence of strain Z4 was based on the genome of *Saccharomyces cerevisiae:*

YORWΔ15:URA3-TPIt-PAL2-TDH3p-ADH1p-C4H-PGI1t-ADH1t-4CL2-PGKp-TEF2p-HCT-CYC1t

YORWΔ17:TEF1p-hphNT1-CYC1t-HOG1t-CCoA-oMT1-ENO2p-PYK1p-FerB2-LRP1t-FBA1p-pAMT-ATP15t rDNA:HIS-CYC1p-sahH-ALY2t-ENO2p-SAM2-SCW4t The gene sequence of strain Z7 was based on the genome of *Saccharomyces cerevisiae:*

YORWΔ15:URA3-TPIt-PAL2-TDH3p-ADH1p-C4H-PGI1t-ADH1t-4CL2-PGKp-TEF2p-HCT-CYC1t

YORWΔ17:TEF1p-hphNT1-CYC1t-HOG1t-CCoA-oMT1-ENO2p-PYK1p-FerB2-LRP1t-FBA1p-pAMT-ATP15t Delta1:LEU-HXT7p-TAL-PRS28At-PFY1p-pheA-PRC1t-HXT7p-Aro9-BAN4t.

rDNA:HIS-CYC1P-sahH-ALY2t-ENO2p-SAM2-SCW4t.

The primer sequences involved in the above were: the promoter and the terminator were both based on the *Saccharomyces cerevisiae* genome as a template, and the special templates were marked below:

Primer 55: 5'>ACCCTGCCCTCATATCACCTGCGTTTCCGTTAAACTATC CTAGTACACTCTATATTTTT<3' (SEQ ID NO: 105), the upstream primer for amplifying the HIS screening marker gene, the underlined sequence was an overlapping sequence with the rDNA site.

Primer 56: 5'>GCCAAGTAGGCAATTATTTAGTACTGTCAGTATTGTTAT CCTGATGCGGTATTTTCTCC<3' (SEQ ID NO: 106), the downstream primer for amplifying the HIS screening marker gene, the underlined sequence was an overlapping sequence with the promoter CYC1p. (Taking the HIS screening marker plasmid purchased from BIOFENG as a template)

Primer 57: 5'>ATACCGCACAGATGCGTAAGGAGAAAATACCGCATCAGG AATTTTTTTGGAAAACCAAG<3' (SEQ ID NO: 107), the upstream primer for CYC1p promoter amplification, the underlined sequence was an overlapping sequence with the HIS screening marker gene.

Primer 58: 5'>GATATCAGCGATTTGTAGTTTTGAGCTGGAGCAGACAT TATTAATTTAGTGTGTGTAT<3' (SEQ ID NO: 108), the downstream primer for CYC1p promoter amplification, the underlined sequence was an overlapping sequence with the gene sahH.

Primer 59: 5'>CTCCTTTATTTGTTCTTTGTCTTTTGACTTCTTCCCGCT ACGCGGCGTTATGTCACTAA<3' (SEQ ID NO: 109), the upstream primer for the amplification of the promoter ENO2p, the underlined sequence was an overlapping sequence with the terminator ALY2t.

Primer 60: 5'>TTCGTTAACAGATTCAGAAGTGAACAAGAAAGTTTCCAT TATTATTGTATGTTATAGTA<3' (SEQ ID NO: 110), the downstream primer for amplification of the promoter ENO2p, the underlined sequence was an overlapping sequence with the gene SAM2.

Primer 61: 5'>GAAGAAGGTCCATTCAAGGCCGACCACTACAGATATTGA TCTAGCACAAGGTTCCTACG<3' (SEQ ID NO: 111), the upstream primer for amplification of the terminator ALY2t, the underlined sequence was an overlapping sequence with the gene sahH.

Primer 62: 5'>CGCAAGTTGGTGCACGTCGTTAGTGACATAACGCCGCGT AGCGGGAAGAAGTCAAAAGA<3' (SEQ ID NO: 112), the downstream primer for amplification of the terminator ALY2t, the underlined sequence was an overlapping sequence with the promoter ENO2p.

Primer 63: 5'>GTTGTTAAGCCATTGAAGTGGGACAAGCCACAAGCTTAA GTCTACTCAATTGTAAAAAA<3' (SEQ ID NO: 113), the upstream primer for terminator SCW4t amplification, the underlined sequence was an overlapping sequence with the gene SAM2.

Primer 64: 5'>AGACTGTCAAGGAGGGTATTCTGGGCCTCCATGTCGCTG CCAAGAGGATCGAGAAACCA<3' (SEQ ID NO: 114), downstream primer for terminator SCW4t amplification, the underlined sequence was an overlapping sequence with the rDNA site.

3) The strains Z4 and Z7 were subjected to fermentation culture using the method of step 7) in Example 1, and the yields of vanillylamine were increased to 9.21 g/L and 14.89 g/L, which showed increases of 47% and 130% on the vanillylamine compared with the unoptimized strains, respectively.

Example 4

Optimizing the SAH hydrolysis pathway, optimizing the regeneration ability of SAM cycle, and improving the synthesis of vanillylamine 1) PCR amplification was conducted on mtn (nucleotide sequence shown in SEQ ID NO: 36) and luxS (nucleotide sequence shown in SEQ ID NO: 37) using two pairs of primers: primers 65 and 66, and primers 67 and 68, respectively, with a genome of *E. coli* as a template. Primers 53 and 54 were used to amplify the gene SAM2 (nucleotide sequence shown in SEQ ID NO: 32) derived from *Arabidopsis thaliana* for encoding SAM synthetase.

The primer sequences involved in the above steps were as follows:

Primer 65: 5'>TTGTCATATATAACCATAACCAAGTAATACATATTCAAA ATGAAAATCGGCATCATTGG<3' (SEQ ID NO: 115), the upstream primer for gene mtn amplification, the underlined sequence was an overlapping sequence with the promoter FBA1p.

Primer 66: 5'>AAAAAAAAAAAAAAATTTTTCAGCCATCTGTTAAGAAAT TTAGCCATGTGCAAGTTTCT<3' (SEQ ID NO: 116), the downstream primer for gene mtn amplification, the underlined sequence was an overlapping sequence with the terminator NAT5t.

Primer 67: 5'>CAAGCTATACCAAGCATACAATCAACTATCTCATATACA ATGCCGTTGTTAGATAGCTT<3' (SEQ ID NO: 117), the upstream primer for gene luxS amplification, the underlined sequence was an overlapping sequence with the promoter ADH1p.

Primer 68: 5'>TGAAAAAAAAAAGTGGTAGATTGGGCTACGTAAATTCGA CTAGATGTGCAGTTCCTGCA<3' (SEQ ID NO: 118), the downstream primer for gene luxS amplification, the underlined sequence was an overlapping sequence with the terminator IDP1t.

2) The amplification was conducted with the following corresponding primers using the genome of *Saccharomyces cerevisiae* as a template, to obtain promoters: FBA1p (nucleotide sequence shown in SEQ ID NO: 18), ADH1p (nucleotide sequence shown in SEQ ID NO: 9); terminators: NAT5t (nucleotide sequence shown in SEQ ID NO: 38), IDP1t (nucleotide sequence shown in SEQ ID NO: 39). The primers 55 and 74, PCR-amplified HIS screening marker gene, and the gene fragments amplified in the above step were assembled into gene expression cassettes according to the processes a to b in step 3) of Example 1: HIS-FBA1p-mtn-NAT5t-ADH1p-luxS-IDP1t. Using primers 73 and 64, the gene expression cassette assembled in Example 3: ENO2p-SAM2-SCW4t template was re-amplified to obtain a new gene expression cassette: ENO2p-SAM2-SCW4t. The above two recombinant gene expression cassettes were transformed into the genomic rDNA sites of Z2 and Z3 strains using the method of step 5) in Example 1, such that an SAH hydrolysis pathway derived from *E. coli* optimized the regeneration ability of SAM in *Saccharomyces cerevisiae*, and Z5 and Z8 strains were formed, respectively.

The gene sequence of strain Z5 was based on the genome of *Saccharomyces cerevisiae:*

YORWΔ15:URA3-TPIt-PAL2-TDH3p-ADH1p-C4H-PGI1t-ADH1t-4CL2-PGKp-TEF2p-HCT-CYC1t

YORWΔ17:TEF1p-hphNT1-CYC1t-HOG1t-CCoA-oMT1-ENO2p-PYK1p-FerB2-LRP1t-FBA1p-pAMT-ATP15t rDNA:HIS-FBA1p-mtn-NAT5t-ADH1p-luxS-IDP1t-ENO2p-SAM2-SCW4t The gene sequence of strain Z8 was based on the genome of *Saccharomyces cerevisiae:*

YORWΔ15:URA3-TPIt-PAL2-TDH3p-ADH1p-C4H-PGI1t-ADH1t-4CL2-PGKp-TEF2p-HCT-CYC1t

YORWΔ17:TEF1p-hphNT1-CYC1t-HOG1t-CCoA-oMT1-ENO2p-PYK1p-FerB2-LRP1t-THS1p-pAMT-MDM35t Delta1:LEU-HXT7p-TAL-PRS28At-PFY1p-pheA-PRC1t-HXT7p-Aro9-BAN4t.

rDNA:HIS-FBA1p-mtn-NAT5t-ADH1p-luxS-IDP1t-ENO2p-SAM2-SCW4t.

The primer sequences involved were: (both promoter and terminator were based on the *Saccharomyces cerevisiae* genome as a template; the special parts were marked below):

Primer 69: 5'>ATACCGCACAGATGCGTAAGGAGAAAATACCGCATCAGG ATAACAATACTGACAGTACT<3' (SEQ ID NO: 119), the upstream primer for the amplification of the promoter FBA1p, the underlined sequence was an overlapping sequence with the HIS screening marker gene.

Primer 70: 5'>AACTTCTTCTTCCATTGCACCAATGATGCCGATTTTCAT TTTGAATATGTATTACTTGG<3' (SEQ ID NO: 120), the downstream primer for the amplification of the promoter FBA1p, the underlined sequence was an overlapping sequence with the gene mtn.

Primer 71: 5'>CAGGTGCAGGCTGACCTAATGGAATTTTTATGGTCCCGA ACATGTAGGTGGCGGAGGGG<3' (SEQ ID NO: 121), the upstream primer for the amplification of promoter ADH1p, the underlined sequence was an overlapping sequence with the terminator NAT5t.

Primer 72: 5'>CCGGGTATGATCGACTGTGAAGCTATCTAACAACGGCAT TGTATATGAGATAGTTGATT<3' (SEQ ID NO: 122), downstream primer for ADH1p promoter amplification, the underlined sequence was an overlapping sequence with the gene luxS.

Primer 73: 5'>CACCGTTTTCTTGAAACCAAACACCGAACTCACTACGCA ACGCGGCGTTATGTCACTAA<3' (SEQ ID NO: 123), the upstream primer for the amplification of the promoter ENO2p-2, the underlined sequence was an overlapping sequence with the terminator IDP1t.

Primer 74: 5'>GCCAAGTAGGCAATTATTTAGTACTGTCAGTATTGTTAT CCTGATGCGGTATTTTCTCC<3' (SEQ ID NO: 124), the downstream primer for amplifying the HIS screening marker gene, the underlined sequence was an overlapping sequence with the promoter FBA1p. (Taking the HIS screening marker plasmid purchased from BIOFENG as a template)

Primer 75: 5'>ATGGTTGAGTCACTGGTGCAGAAACTTGCACATGGCTAA ATTTCTTAACAGATGGCTGA<3' (SEQ ID NO: 125), the upstream primer for the amplification of the terminator NAT5t, the underlined sequence was an overlapping sequence with the gene mtn.

Primer 76: 5'>TCTGTTCTATTGTATATCTCCCCTCCGCCACCTACATGT TCGGGACCATAAAAATTCCA<3' (SEQ ID NO: 126), downstream primer for terminator NAT5t amplification, the underlined sequence was an overlapping sequence with the promoter ADH1p.

Primer 77: 5'>GCACTGCCGAAAGAGAAGTTGCAGGAACTGCACATCTAG TCGAATTTACGTAGCCCAAT<3' (SEQ ID NO: 127), the upstream primer for amplification of the terminator IDP1t, the underlined sequence was an overlapping sequence with the gene luxS.

Primer 78: 5'>CGCAAGTTGGTGCACGTCGTTAGTGACATAACGCCGCGT TGCGTAGTGAGTTCGGTGTT<3' (SEQ ID NO: 128), the downstream primer for amplification of the terminator IDP1t, the underlined sequence was an overlapping sequence with the promoter ENO2p.

3) The strains Z5 and Z8 were subjected to fermentation culture using the method of step 7) in Example 1, and the yields of vanillylamine were increased to 11.88 g/L and 16.48 g/L, which showed increases of 84% and 160% on the vanillylamine compared with the unoptimized strains, respectively.

Figure 2:
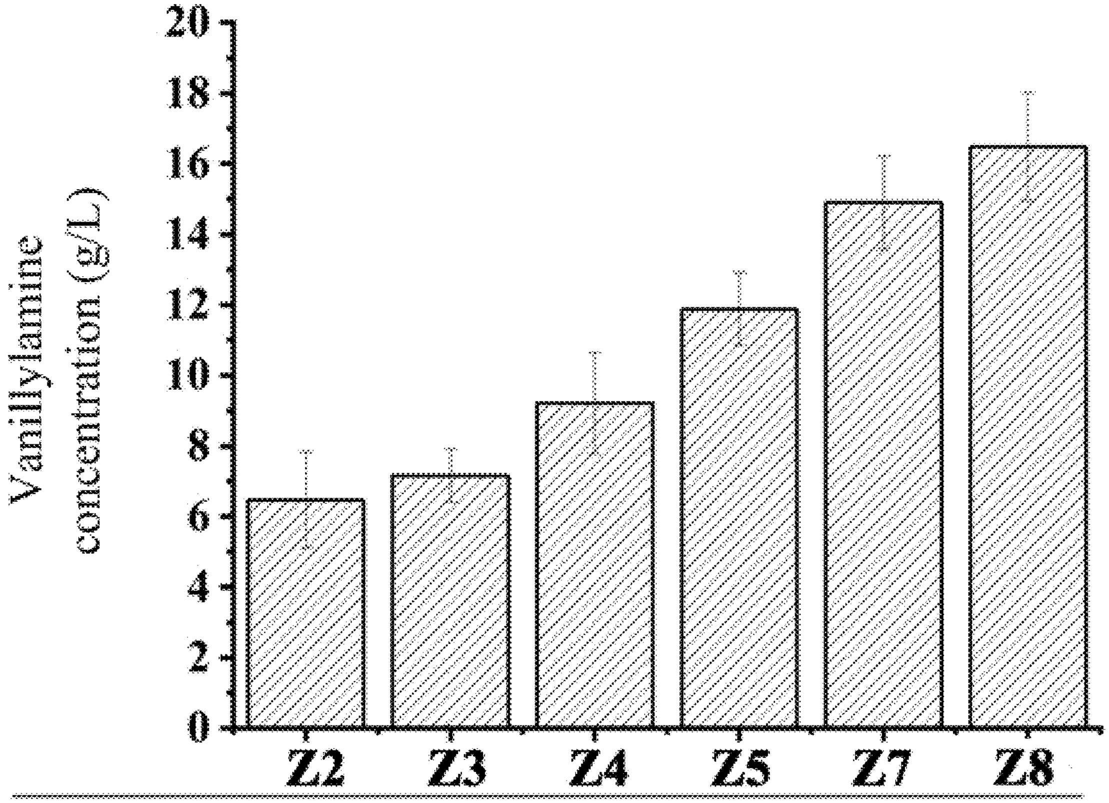
FIG. 2 shows output results of the vanillylamine of engineered *Saccharomyces cerevisiae* strains constructed in Examples 1 to 4.

The comparative results of the vanillylamine yields of the engineered *Saccharomyces cerevisiae* strains obtained in Examples 1 to 4 were shown in FIG. 2.

Example 5

Construction of engineered *Saccharomyces cerevisiae* strains for capsaicin synthesis 1) According to the method in step 2) of Example 1, two head-to-head promoter modules were constructed: pBM16A-PGK1p+FBA1p and pBM16A-GPM1p (nucleotide sequence shown in SEQ ID NO: 40)+ACT1p. Two back-to-back terminator modules were chemically synthesized by GENEWIZ: ASP3t (nucleotide sequence shown in SEQ ID NO: 41)-HAP4t (nucleotide sequence shown in SEQ ID NO: 49), and YCP4t (nucleoside sequence shown in SEQ ID NO: 50)--MDM35t (nucleotide sequence shown in SEQ ID NO: 42). The Δ22site1 plasmid (nucleotide sequence shown in SEQ ID NO: 43) of the upper sequence of YORWΔ22 site and the Δ22site2 plasmid (nucleotide sequence shown in SEQ ID NO: 44) of the lower sequence of YORWΔ22 site, containing G-418 resistance, were selected; the Δ22site1 and Δ22site2 plasmids were prepared using the c to g processes of step 2) in Example 1.
2) PCR amplification was conducted on the promoter module, and functional genes Kas (nucleotide sequence shown in SEQ ID NO: 45), Acl (nucleotide sequence shown in SEQ ID NO: 46), Fat (nucleotide sequence shown in SEQ ID NO: 47), and AT3 (the nucleotide sequence shown in SEQ ID NO: 48). Two double transformation units were assembled using the Golden Gate method: DH5α/PUC57T-(ASP3t-Kas-PGK1p-FBA1p-Acl-HAP4t) and DH5α/PUC57T-(YCP4t-Fat-GPM1p-ACT1p-AT3-MDM35t). Through method of step 5) in Example 1, the four genes were constructed on the genome of the Z2 strain to realize heterologous expression of the capsaicin pathway in *Saccharomyces cerevisiae*. The resulting strain was named C1.

The gene sequence of strain C1 was based on the genome of *Saccharomyces cerevisiae:*

YORWΔ15:URA3-TPIt-PAL2-TDH3p-ADH1p-C4H-PGI1t-ADH1t-4CL2-PGKp-TEF2p-HCT-CYC1t

YORWΔ17:TEF1p-hphNT1-CYC1t-HOG1t-CCoA-oMT1-ENO2p-PYK1p-FerB2-LRP1t-FBA1p-pAMT-ATP15t YORWΔ22:TEF1p-KanMX-TEF1t-ASP3t-Kas-PGK1p-FBA1p-Acl-HAP4t-YCP4t-Fat-GPM1p-ACT1p-AT3-MDM35t The primer sequences involved in the process were as follows: (the promoter used the *Saccharomyces cerevisiae* genome as a template; the gene used a synthetic plasmid as a template)

Primer 79: 5'>CCTGCTCTTCACATTGTTTTATATTTGTTGTAAAAAGTAG<3' (SEQ ID NO: 129), the upstream primer for amplification of the promoter PGK1p, the underlined sequence was a cohesive end formed by the digestion of the promoter PGK1p by Sap1.

Primer 80: 5'>GCCAAGTAGGCAATTATTTAGTACTGTCAGTATTGTTAT ACGCACAGATATTATAACAT<3' (SEQ ID NO: 130), the downstream primer for the amplification of the promoter PGK1p, the underlined sequence was an overlapping sequence with the promoter FBA1p.

Primer 81: 5'>GCAAATGCCTATTGTGCAGATGTTATAATATCTGTGCGT ATAACAATACTGACAGTACT<3' (SEQ ID NO: 131), the upstream primer for the amplification of the promoter FBA1p, the underlined sequence was an overlapping sequence with the promoter PGK1p.

Primer 82: 5'>CCTGCTCTTCATGTTTTGAATATGTATTACTTGGTTATG<3' (SEQ ID NO: 132), the downstream primer for the amplification of promoter FBA1p, the underlined sequence was a cohesive end formed after the promoter FBA1p was digested by Sap1.

Primer 83: 5'>CCTGCTCTTCACATATTGTAATATGTGTGTTTGTTTGG<3' (SEQ ID NO: 133), the upstream primer for the amplification of promoter GPM1p, the underlined sequence was a cohesive end formed after the promoter GPM1p was digested by Sap1.

Primer 84: 5'>ATTATATTATATGGGTCTGCAAGGTAGAGGCGCGCTTGT CACATGCAGTGATGCACGCG<3' (SEQ ID NO: 134), the downstream primer for the amplification of promoter GPM1p, the underlined sequence was an overlapping sequence with the promoter ATC1p.

Primer 85: 5'>ATGTAACTTAGCACCATCGCGCGTGCATCACTGCATGTG ACAAGCGCGCCTCTACCTTG<3' (SEQ ID NO: 135), the upstream primer for the amplification of the promoter ATC1p, the underlined sequence was an overlapping sequence with the promoter GPM1p.

Primer 86: 5'>CCTGCTCTTCATGTTGTTAATTCAGTAAATTTTCGATC<3' (SEQ ID NO: 136), the downstream primer for the amplification of promoter ATC1p, the underlined sequence was a cohesive end formed after the promoter ATC1p was digested by Sap1.

Primer 87: 5'>CCTGCTCTTCAGGT TTATGGCTTGTATGGGGCGAAGAC<3' (SEQ ID NO: 137), the upstream primer for gene Kas amplification, the underlined sequence was a cohesive end of gene Kas after Sap1 digestion.

Primer 88: 5'>CCTGCTCTTCAGTA ATGTCTTCTATCACTTCTTCTTG<3' (SEQ ID NO: 138), the downstream primer for gene Kas amplification, the underlined sequence was a cohesive end of gene Kas after Sap1 digestion.

Primer 89: 5'>CCTGCTCTTCAACA ATGGCTTCTATCACTGCTTCTTCTTTC<3' (SEQ ID NO: 139), the upstream primer for gene Acl amplification, the underlined sequence was a cohesive end formed after gene Acl was digested by Sap1.

Primer 90: 5'>CCTGCTCTTCAGAT TTAACACTTCTTAGCAACCAAGTCTTC<3' (SEQ ID NO: 140), downstream primer for gene Acl amplification, the underlined sequence was a cohesive end of gene Acl after Sap1 digestion.

Primer 91: 5'>CCTGCTCTTCAGGTTTAGATTCTAGATGGCTTCTTTC<3' (SEQ ID NO: 141), the upstream primer for gene Fat amplification, the underlined sequence was a cohesive end of gene Fat after Sap1 digestion.

Primer 92: 5'>CCTGCTCTTCAGTAATGTTGTCTAGAGGTTCTTTCTTG<3' (SEQ ID NO: 142), the downstream primer for gene Fat amplification, the underlined sequence was a cohesive end of gene Fat after Sap1 digestion.

Primer 93: 5'>CCTGCTCTTCAACAATGGCTTTCGCTTTGCCATCTTC<3' (SEQ ID NO: 143), the upstream primer for geneAT3 amplification, the underlined sequence was a cohesive end of gene AT3 after Sap1 digestion.

Primer 94: 5'>CCTGCTCTTCAGATTTAAGCGATGAATTCAACCAATTC<3' (SEQ ID NO: 144), the downstream primer for gene AT3 amplification, the underlined sequence was a cohesive end of gene AT3 after Sap1 digestion.

Figure 3A:
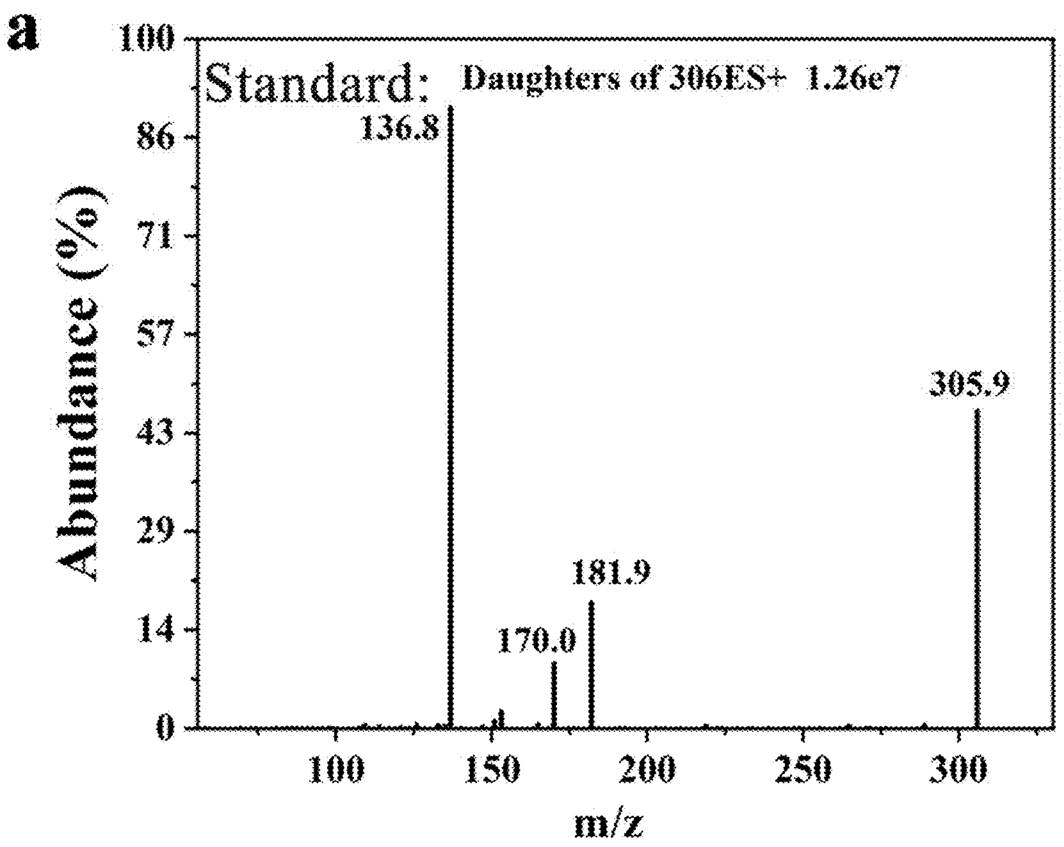
FIG. 3A and FIG. 3B show HPLC-MS/MS quantitative analysis results of capsaicin produced by the fermentation of the C1 strain.
Figure 3B:
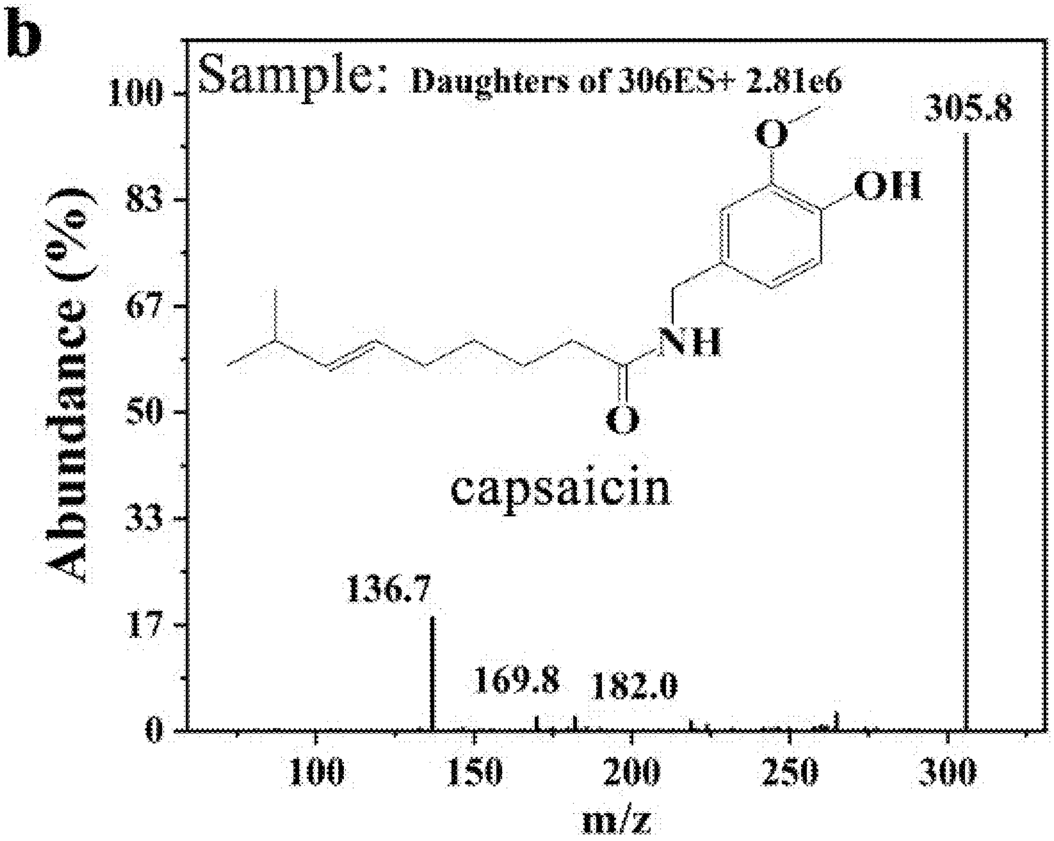

3) The strain C1 was subjected to fermentation culture using the method of step 7) in Example 1, and the culture time was extended to 120 h. After the fermentation, 100 mL of a fermentation broth was subjected to centrifugation at 5000 rpm for 5 min to collect the bacterial cells. The cells were washed twice with clean water to remove residual fermentation broth, re-centrifuged to collect the bacterial cells, 10 mL of an organic extract (ethyl acetate: n-butanol=3:1) was added to the centrifuge tube to resuspend the bacterial cells. An appropriate amount of glass beads were added, and the cells were vortexed for 30 min to ensure that the cells were fully lysed. An obtained cell lysate was re-centrifuged to obtain a supernatant, which was concentrated to 1 mL by rotary evaporation. A resulting concentrate was qualitatively and quantitatively analyzed using HPLC-MS/MS. The results were shown in FIGS. 3A-3B, and it was found that the yield of capsaicin in the strain C1 was 80.23 μg/L. In the present disclosure, the de novo biosynthesis of capsaicin in *Saccharomyces cerevisiae* was realized for the first time.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. An engineered *Saccharomyces cerevisiae*, comprising a gene module 1 and a gene module 2; wherein the gene module 1 comprises PAL2, C4H, 4CL2, and HCT genes, and the gene module 2 comprises CCoAoMT1, FerB2, and pAMT genes; and wherein the PAL2 gene has the nucleotide sequence shown in SEQ ID NO: 1, the C4H gene has the nucleotide sequence shown in SEQ ID NO: 2, the 4CL2 gene has the nucleotide sequence shown in SEQ ID NO: 3, the HCT gene has the nucleotide sequence shown in SEQ ID NO: 4, the CCoAoMT1 gene has the nucleotide sequence shown in SEQ ID NO: 5, the FerB2 gene has the nucleotide sequence shown in SEQ ID NO: 6, and the pAMT gene has the nucleotide sequence shown in SEQ ID NO: 7.

2. The engineered *Saccharomyces cerevisiae*, according to claim 1, further comprising pheA, Aro9, and TAL genes integrated therein; wherein said pheA gene has the nucleotide sequence shown in SEQ ID NO: 22, the Aro9 gene has the nucleotide sequence shown in SEQ ID NO: 23, and the TAL gene has the nucleotide sequence shown in SEQ ID NO: 28.

3. An engineered *Saccharomyces cerevisiae* for production of vanillylamine, obtained by inserting SahH and SAM2 genes into the engineered *Saccharomyces cerevisiae* according to claim 2; wherein the SahH gene has the nucleotide sequence shown in SEQ ID NO: 31, and the SAM2 gene has the nucleotide sequence shown in SEQ ID NO: 32.

4. An engineered *Saccharomyces cerevisiae*, comprising the engineered *Saccharomyces cerevisiae* of claim 2 with mtn, luxS, and SAM2 genes integrated therein; wherein the mtn gene has the nucleotide sequence shown in SEQ ID NO: 36, the luxS gene has the nucleotide sequence shown in SEQ ID NO: 37, and the SAM2 gene has the nucleotide sequence shown in SEQ ID NO: 32.

5. An engineered *Saccharomyces cerevisiae*, comprising the engineered *Saccharomyces cerevisiae* of claim 2 with Kas, Acl, Fat, and AT3 genes integrated therein; wherein the Kas gene has the nucleotide sequence shown in SEQ ID NO: 45, the Acl gene has the nucleotide sequence shown in SEQ ID NO: 46, the Fat gene has the nucleotide sequence shown in SEQ ID NO: 47, and the AT3 gene has the nucleotide sequence shown in SEQ ID NO: 48.

6. A method for constructing the engineered *Saccharomyces cerevisiae* according to claim 2, comprising the following steps: constructing two gene expression cassettes of PFY1p-pheA-PRC1t-ACT1p-Aro9-BAN4t and HXT7p-TAL-PRS28At, and inserting said two gene expression cassettes jointly into a delta1 site of a genome of a *Saccharomyces cerevisiae* comprising the gene module 1 and the gene module 2; wherein PFY1p has the nucleotide sequence shown in SEQ ID NO: 24, ACT1p has the nucleotide sequence shown in SEQ ID NO: 25, PRC1t has the nucleotide sequence shown in SEQ ID NO: 26, BAN4t has the nucleotide sequence shown in SEQ ID NO: 27, HXT7p has the nucleotide sequence shown in SEQ ID NO: 29, and PRS28At has the nucleotide sequence shown in SEQ ID NO: 30.

7. An engineered *Saccharomyces cerevisiae* for production of vanillylamine, obtained by inserting SahH and SAM2 genes into the engineered *Saccharomyces cerevisiae* according to claim 1; wherein the SahH gene has the nucleotide sequence shown in SEQ ID NO: 31, and the SAM2 gene has the nucleotide sequence shown in SEQ ID NO: 32.

8. An engineered *Saccharomyces cerevisiae* for production of capsaicin, obtained by inserting Kas, Acl, Fat, and AT3 genes into the engineered *Saccharomyces cerevisiae* according to claim 7; wherein the Kas gene has the nucleotide sequence shown in SEQ ID NO: 45, the Acl gene has the nucleotide sequence shown in SEQ ID NO: 46, the Fat gene has the nucleotide sequence shown in SEQ ID NO: 47, and the AT3 gene has the nucleotide sequence shown in SEQ ID NO: 48.

9. A method for constructing the engineered *Saccharomyces cerevisiae* according to claim 7, comprising the following steps: constructing two gene expression cassettes of HIS-CYC1p-SahH-ALY2t and ENO2p-SAM2-SCW4t, and inserting the two gene expression cassettes into an rDNA site of a genome of the engineered *Saccharomyces cerevisiae*, wherein two gene modules are inserted into the engineered *Saccharomyces cerevisiae*; a gene module 1 comprises PAL2, C4H, 4CL2, and HCT genes, and a gene module 2 comprises CCoAoMT1, FerB2, and pAMT genes; and the PAL2, C4H, and 4CL2 genes are derived from *Arabidopsis thaliana*, the HCT and CCoAoMT1 genes are derived from *Nicotiana tabacum*, the FerB2 gene is derived from *Sphingomonas paucimobilis*, and the pAMT gene is derived from *Capsicum annuum*; wherein CYC1p has the nucleotide sequence shown in SEQ ID NO: 33, ENO2p has the nucleotide sequence shown in SEQ ID NO: 16, ALY2t has the nucleotide sequence shown in SEQ ID NO: 34, and SCW4t has the nucleotide sequence shown in SEQ ID NO: 35.

10. The engineered *Saccharomyces cerevisiae*, according to claim 1, further comprising mtn, luxS, and SAM2 genes integrated therein; wherein the mtn gene has the nucleotide sequence shown in SEQ ID NO: 36, the luxS gene has the nucleotide sequence shown in SEQ ID NO: 37, and the SAM2 gene has the nucleotide sequence shown in SEQ ID NO: 32.

11. An engineered *Saccharomyces cerevisiae*, comprising the engineered *Saccharomyces cerevisiae* of claim 10 with Kas, Acl, Fat, and AT3 genes integrated therein; wherein the Kas gene has the nucleotide sequence shown in SEQ ID NO: 45, the Acl gene has the nucleotide sequence shown in SEQ ID NO: 46, the Fat gene has the nucleotide sequence shown in SEQ ID NO: 47, and the AT3 gene has the nucleotide sequence shown in SEQ ID NO: 48.

12. A method for constructing the engineered *Saccharomyces cerevisiae* according to claim 10, comprising the following steps: constructing two gene expression cassettes of HIS-FBA1p-mtn-NAT5t-ADH1p-luxS-IDP1t and ENO2p-SAM2-SCW4t, and inserting the two gene expression cassettes into an rDNA site of a genome of the *Saccharomyces cerevisiae* comprising the gene module 1 and the gene module 2; wherein NAT5t has the nucleotide sequence shown in SEQ ID NO: 38, and IDP1t has the nucleotide sequence shown in SEQ ID NO: 39.

13. An engineered *Saccharomyces cerevisiae* for production of capsaicin, obtained by inserting Kas, Acl, Fat, and AT3 genes into the engineered *Saccharomyces cerevisiae* according to claim 1; wherein the Kas gene has the nucleotide sequence shown in SEQ ID NO: 45, the Acl gene has the nucleotide sequence shown in SEQ ID NO: 46, the Fat gene has the nucleotide sequence shown in SEQ ID NO: 47, and the AT3 gene has the nucleotide sequence shown in SEQ ID NO: 48.

14. A method for constructing the engineered *Saccharomyces cerevisiae* according to claim 13, comprising the following steps: constructing two double transformation units of ASP3t-Kas-PGK1p-FBA1p-Acl-HAP4t and YCP4t-Fat-GPM1p-ACT1p-AT3-MDM35t, and inserting the two double transformation units into a YORWΔ22 site of a genome of the engineered *Saccharomyces cerevisiae*, wherein two gene modules are inserted into the engineered *Saccharomyces cerevisiae*; a gene module 1 comprises PAL2, C4H, 4CL2, and HCT genes, and a gene module 2 comprises CCoAoMT1, FerB2, and pAMT genes; and the PAL2, C4H, and 4CL2 genes are derived from *Arabidopsis thaliana*, the HCT and CCoAoMT1 genes are derived from *Nicotiana tabacum*, the FerB2 gene is derived from *Sphingomonas paucimobilis*, and the pAMT gene is derived from *Capsicum annuum*; wherein ASP3t has the nucleotide sequence shown in SEQ ID NO: 41, HAP4t has the nucleotide sequence shown in SEQ ID NO: 49, YCP4t has the nucleotide sequence shown in SEQ ID NO: 50, and MDM35t has the nucleotide sequence shown in SEQ ID NO: 42.

15. A method for constructing the engineered *Saccharomyces cerevisiae* according to claim 1, comprising the following steps:

constructing two double transformation units of TPI1t-PAL2-TDH3p-ADH1p-C4H-PGI1t and ADH1t-4CL2-PGK1p-TEF2p-HCT-CYC1t, and inserting the two double transformation units into a YPRCΔ15 site of a genome of *Saccharomyces cerevisiae* to obtain a strain Z1; and constructing a gene expression cassette FBA1p-pAMT-ATP15t and a double transformation unit HOG1t-CCoAoMT1-ENO2p-PYK1p-FerB2-LRP1t, and inserting the gene expression cassette and the double transformation unit jointly into a YORWΔ17 site of a genome of the strain Z1; wherein TDH3p has the nucleotide sequence shown in SEQ ID NO: 8, ADH1p has the the nucleotide sequence shown in SEQ ID NO: 9, PGK1p has the nucleotide sequence shown in SEQ ID NO: 10, TEF2p has the nucleotide sequence shown in SEQ ID NO: 11, TPI1t has the nucleotide sequence shown in SEQ ID NO: 12, PGI1t has the nucleotide sequence shown in SEQ ID NO: 13, ADH1t has the nucleotide sequence shown in SEQ ID NO: 14, CYC1t has the nucleotide sequence shown in SEQ ID NO: 15, ENO2p has the nucleotide sequence shown in SEQ ID NO: 16, PYK1p has the nucleotide sequence shown in SEQ ID NO: 17, FBA1p has the nucleotide sequence shown in SEQ ID NO: 18, HOG1t has the nucleotide sequence shown in SEQ ID NO: 19, LRP1t has the nucleotide sequence shown in SEQ ID NO: 20, and ATP15t has the nucleotide sequence shown in SEQ ID NO: 21.

* * * * *